United States Patent [19]

Bissett et al.

[11] Patent Number: 5,487,884

[45] Date of Patent: Jan. 30, 1996

[54] PHOTOPROTECTION COMPOSITIONS COMPRISING CHELATING AGENTS

[75] Inventors: Donald L. Bissett, Hamilton; Rodney D. Bush, Cincinnati; Ranjit Chatterjee, Fairfield, all of Ohio

[73] Assignee: The Procter & Gamble Company, Cincinnati, Ohio

[21] Appl. No.: 86,757

[22] Filed: Jul. 1, 1993

Related U.S. Application Data

[63] Continuation of Ser. No. 619,805, Nov. 27, 1990, abandoned, which is a continuation of Ser. No. 251,910, Oct. 4, 1988, abandoned, which is a continuation-in-part of Ser. No. 112,576, Oct. 22, 1987, abandoned.

[51] Int. Cl.$^6$ .............................. A61K 7/06; A61K 7/42; A61K 7/48; A61K 7/50
[52] U.S. Cl. .......................... 424/59; 252/106; 252/107; 424/DIG. 5; 424/47; 424/60; 424/70.9; 514/844; 514/845; 514/846; 514/847
[58] Field of Search .............................. 514/640; 424/59

[56] References Cited

U.S. PATENT DOCUMENTS

| | | | |
|---|---|---|---|
| 4,000,276 | 12/1976 | Hasunuma et al. | 424/251 |
| 4,098,881 | 7/1978 | Majeti | 424/59 |
| 4,144,325 | 3/1979 | Voyt | 424/59 |
| 4,185,100 | 1/1980 | Rovee et al. | 424/240 |
| 4,248,861 | 2/1981 | Schutt | 424/60 |
| 4,264,581 | 4/1981 | Kerkhof et al. | 424/60 |
| 4,338,293 | 6/1982 | Holick | 424/59 |
| 4,528,196 | 7/1985 | Pitt | 514/533 |
| 4,579,844 | 4/1986 | Rovee et al. | 514/171 |
| 4,603,146 | 7/1986 | Kligman | 514/559 |
| 4,673,692 | 6/1987 | Suzuki et al. | 514/640 |
| 4,816,487 | 3/1989 | Schewe et al. | 514/640 |

FOREIGN PATENT DOCUMENTS

| | | | |
|---|---|---|---|
| 0149242 | 7/1985 | European Pat. Off. | 514/640 |
| 0166221 | 1/1986 | European Pat. Off. | A61K 7/42 |
| 0185158 | 6/1986 | European Pat. Off. | 514/640 |
| 0265400 | 4/1988 | European Pat. Off. | A61K 47/00 |
| 0308543 | 3/1989 | European Pat. Off. | A61K 7/42 |
| 0308919 | 3/1989 | European Pat. Off. | A61K 7/42 |
| 2596986 | 10/1987 | France | A61K 7/48 |
| 2641696 | 7/1990 | France | A61K 7/48 |
| 2461039 | 6/1976 | Germany | 514/640 |
| 2517216 | 10/1976 | Germany | A61K 7/00 |
| 3140954 | 5/1983 | Germany | A61K 31/44 |
| 53-06432 | 1/1978 | Japan | A61K 7/00 |
| 53-03538 | 1/1978 | Japan | A61K 7/48 |
| 0087757 | 7/1980 | Japan | 514/640 |
| 55-157509 | 12/1980 | Japan | A61K 7/42 |
| 58-113115 | 7/1983 | Japan | A61K 7/48 |
| 58-222007 | 12/1983 | Japan | A61K 7/00 |
| 59-10506 | 1/1984 | Japan | A61K 7/00 |
| 59-25897 | 2/1984 | Japan | C11D 3/16 |
| 59-170011 | 9/1984 | Japan | A61K 7/42 |
| 61-143311 | 12/1984 | Japan | A61K 7/00 |
| 61-197506 | 9/1986 | Japan | A61K 7/00 |
| 61-215314 | 9/1986 | Japan | A61K 7/42 |
| 61-215313 | 9/1986 | Japan | A61K 7/42 |
| 62-108804 | 5/1987 | Japan | A61K 7/00 |
| 64-66117 | 3/1989 | Japan | A61K 31/165 |
| 348210 | 9/1972 | U.S.S.R. | 514/640 |
| 559089 | 2/1944 | United Kingdom | 514/277 |
| 901648 | 7/1962 | United Kingdom | 424/59 |
| 986368 | 3/1965 | United Kingdom | 424/59 |
| 1457495 | 12/1976 | United Kingdom | C07D 213/66 |
| 2208149 | 3/1989 | United Kingdom | A61K 7/48 |

OTHER PUBLICATIONS

Guerney, P. J., R. J. Knight & R. N. Sylva, "Temperature Dependence of the Formation of Tris[2,3–bis(2–pyridyl)–pyrazineliron(II)", Aust. J. Chem., vol. 27, No. 12 (1974), pp. 2671–2675 (Abstract Only).

Goldschmiedt, H., "Vitamin E in Cosmetics", Soap/Cosmetics/Chemical Specialties, vol. 48, No. 8 (Aug., 1972), pp. 40, 42.

Graf, E., J. R. Mahoney, R. G. Bryant & J. W. Eaton, "Iron–catalyzed Hydroxyl Radical Formation. Stringent Requirement for Free Iron Coordination Site", J. Biol. Chem., vol. 259, No. 6 (1984), pp. 3620–3624.

Hatefi, Y. & W. G. Hanstein, "Lipid Oxidation in Biological Membranes. I. Lipid Oxidation in Submitochondrial Particles and Microsomes Induced by Chaotropic Agents", Archives of Biochemistry and Biophysics, vol. 138 (1970), pp. 73–86.

Kontoghiorghes, G. J., "Iron Mobilisation from Lactoferrin by Chelators at Physiological pH", Biochimica et Biophysica Acta, vol. 882 (1986), pp. 267–270.

Patch, M. G., K. P. Simolo & C. J. Carrano, "Evaluation of Iron(III) N,N'–Ethylenebis(o–hydroxyphenyl)glycinate) as a Model for the Iron Binding Site in the Transferrins", Inorg. Chem., vol. 22 (1983), pp. 2630–2634.

Ponka, P., R. W. Grady, A. Wilczynska & H. M. Schulman, "The Effect of Various Chelating Agents on the Mobilization of Iron from Reticulocytes in the Presence and Absence of Pyridoxal Isonicotinoyl Hydrazone", Biochimica et Biophysica Acta, vol. 802 (1984), pp. 477–489.

Sassaki, Y., "Synergistic Extraction and Spectrophotometric Determination of Iron(II) with α–Furildioxime and Butylamine", Bunseki Kagaku, vol. 30, No. 1 (1981), pp. 35–39, (Abstract Only).

Betts, W. H., M. W. Whitehouse, L. G. Cleland & B. Vernon–Roberts, "In Vitro Antioxidant Properties of Potential Biotransformation Products of Salicylate, Sulphasalazine and Amidopyrine", Journal of Free Radicals in Biology & Medicine, vol. 1 (1985), pp. 273–280.

(List continued on next page.)

Primary Examiner—Dale R. Ore
Attorney, Agent, or Firm—Milton B. Graff; David L. Suter; Jerry J. Yetter

[57] ABSTRACT

The present invention involves photoprotective compositions which are useful for topical application to prevent damage to skin caused by acute or chronic exposure to ultraviolet light comprising chelating agents. Also involved are compositions comprising chelating agents together with anti-inflammatory agents, sunscreening agents, and/or radical scavenging agents. Methods for using such compositions to prevent damage to skin caused by acute or chronic exposure to ultraviolet light are also involved.

25 Claims, No Drawings

OTHER PUBLICATIONS

Bors, W., M. Saran & C. Michel, "Pulse–radiolytic Investigations of Catechols and Catecholamines. II. Reactions of Tiron with Oxygen Radical Species", Biochim. Biophys. Acta, vol. 582, No. 3 (1979), pp. 537–542. (Abstract Only).

Burbridge, C. D. & D. M. L. Goodgame, "Di–2–pyridylamine Complexes of Iron(II)", J. Chem. Soc., vol. 4 (1967), pp. 694–697. (Abstract Only).

Foye, W. O. & J. Mickles, "Antiradiation Compounds. II. Dithiocarbamates", Journal of Medicinal and Pharmaceutical Chemistry, vol. 5, No. 4 (Jul. 23, 1962), pp. 846–852.

Davies, K. J. A., "Protein Damage and Degradation by Oxygen Radicals", *The Journal of Biological Chemistry*, vol. 262, No. 20 (1987), pp. 9895–9901.

Black, H. S., "Potential Involvement of Free Radical Reactions in Ultraviolet Light–Mediated Cutaneous Damage", *Photochemistry and Photobiology*, vol. 45, No. 2, (1987), pp. 213–221.

Braughler, Duncan & Chase, "The Involvement of Iron in Lipid Peroxidation", *The Journal of Biological Chemistry*, vol. 22 (1986), pp. 10282–10289.

Nunez, Cole & Glass, "The Reticulocyte Plasma Membrane Pathway of Iron Uptake as Determined by the Mechanism of $\alpha,\alpha'$–Dipyridyl Inhibition", *The Journal of Biological Chemistry*, vol. 258, No. 2 (1983), pp. 1145–1151.

DeMello Filho & Meneghini, "Protection of Mammalian Cells by o–Phenanthroline from Lethal and DNA–damaging Effects Produced by Active Oxygen Species", *Biochemica et Biophysica Acta*, vol. 847 (1985), pp. 82–89.

Ramos Arrocha, Morales Lacarrere, Quintero, Lopez Guerra & Planas de la Torre, "Solución technológica al problema de la contaminación microbiana en loción antisolar (emulsion)", *Rev. Cubana Farm.*, vol. 18, No. 1 (1984) pp. 27–34.

Law & Lewis, "The Effect of Systemically and Topically Applied Drugs on Ultraviolet Induced Erythema in the Rat", *British Journal of Pharmacology*, vol. 59, No. 4 (1977), pp. 591–597.

Kaidbey & Kurban, "The Influence of Corticosteroids and Topical Indomethacin on Sunburn Erythema", *The Journal of Investigative Dermatology*, vol 66, (1976), pp. 153–156.

Gruber, Ridolfo, Nickander & Mikulaschek, "Delay of Erythema of Human Skin by Anti–Inflammatory Drugs After Ultraviolet Irradiation", *Clinical Pharmacology and Therapeutics*, vol. 13, No. 1 (1971), pp. 109–113.

Hart, "Chelating Agents in Cosmetic and Toiletry Products", *Cosmetics and Toiletries,* vol. 93, No. 12 (1978, pp. 28–30.

Hart, "EDTA–Type Chelating Agents in Personal Care Products" *Cosmetics and Toiletries*, vol. 98, No. 4 (1983), pp. 54–58.

Woolley, Glanville, Roberts & Evanson, "Purification, Characterization and Inhibition of Human Skin Collagenase", *Biochemistry Journal*, vol. 169 (1978), pp. 265–276.

Stevens, R. G., D. Y. Jones, M. S. Micozzi & P. R. Taylor, "Body Iron Stores and the Risk of Cancer", *New England Journal of Medicine* , vol. 319, No. 16 (1988), pp. 1047–1502.

Hann, H. L., M. W. Stahlhut & B. S. Blumberg, "Iron Nutrition and Tumor Growth: Decreased Tumor Growth in Iron–deficient Mice", *Cancer Research*, vol. 48 (1988), pp. 4168–4170.

Ackerman, Z., M. Seidenbaum, E. Loewenthal & A. Rubinow, "Overload of Iron in the Skin of Patients with Varicose Ulcers", *Archives of Dermatology*, vol. 124 (Sep., 1988), pp. 1376–1378.

Gorodetsky, R., J. Sheskin & A. Weinreb, "Iron, Copper, and Zinc Concentrations in Normal Skin and in Various Nonmalignant and Malignant Lesions", *International Journal of Dermatology*, vol. 25, No. 7 (Sep., 1986), pp. 440–445.

Merck Index, 1976, 9th edition, p. 555.

PHOTOPROTECTION COMPOSITIONS COMPRISING CHELATING AGENTS

This is a continuation of patent application Ser. No. 619,805, filed on Nov. 27, 1990, now abandoned, which is a continuation of patent application Ser. No. 251,910, filed on Oct. 4, 1988, now abandoned, which is a continuation-in-part of patent application Ser. No. 112,576, filed on Oct. 22, 1987, now abandoned.

TECHNICAL FIELD

This invention relates to topical compositions useful for protecting the skin from the harmful effects of ultraviolet irradiation, such as sunburn and sun-induced premature aging of the skin.

BACKGROUND OF THE INVENTION

Sunbathing is a popular activity worldwide. A suntan is associated with health, beauty, status and wealth. Many leisure-time activities, such as swimming, tennis, golf, and fishing, are done in the sun. Furthermore, many people are forced to be in the sun for long periods of time due to their occupation.

However, the damaging effects of sunlight on skin are well documented. Contrary to what most people believe, it is not necessary that one sunbathe to suffer the ill-effects of excessive UV exposure. In fact, a lot of damage can be done just by routine day-to-day activities in the sunlight. Some scientists estimate that over 70 percent of the damage the sun inflicts on the average person's skin over a lifetime is the result of simply being outdoors or even sitting by a window.

The major short term hazard of prolonged exposure to sunlight is erythema (i.e., sunburn). The 290 to 320 nanometer wavelength ultraviolet radiation range, designated as the "UVB" wavelength range, tends to be the primary cause of erythema. The 320 to 400 nanometer wavelength ultraviolet radiation range, designated as the "UVA" wavelength range, also produces erythema.

In addition to the short term hazard of erythema, there are also long term hazards associated with UV radiation exposure. One of these long term hazards is malignant changes in the skin surface. Numerous epidemiologic studies demonstrate a strong relationship between sunlight exposure and human skin cancer. Another long term hazard of ultraviolet radiation is premature aging of the skin. This condition is characterized by wrinkling and yellowing of the skin, along with other physical changes such as cracking, telangiectasis (spider vessels), solar keratoses (growths), ecchymoses (subcutaneous hemorrhagic lesions), and loss of elasticity (sagging). The adverse effects associated with exposure to UVA and UVB wavelength radiation are more fully discussed in DeSimone, "Sunscreen and Suntan Products", *Handbook of Nonprescription Drugs*, 7th Ed, Chapter 26, pp. 499–511 (American Pharmaceutical Association, Washington, D.C.; 1982); Grove and Forbes, "A Method for Evaluating the Photoprotection Action of Sunscreen Agents Against UV-A Radiation", *International Journal of Cosmetic Science*, 4, pp. 15–24 (1982); and U.S. Pat. No. 4,387,089, DePolo, issued Jun. 7, 1983; the disclosures of all of which are incorporated herein by reference. Hence, although the immediate effects of ultraviolet radiation may be cosmetically and socially gratifying, the long-term hazards are cumulative and potentially serious.

The fact that these effects are taken seriously by the general public is suggested by considering the sun protection products' market. This market has grown considerably in recent years and many new products are introduced each year. What used to be looked upon as a seasonal business is no longer. Sun protection compounds are now included in a diversity of personal care products, particularly cosmetic-type products which are worn on a daily basis.

Obviously the most effective way to avoid excessive UV exposure is to simply refrain from being out in the sun. This is not only an impractical solution but an impossible one for those who work out-of-doors. Furthermore, some effects of exposure to sunlight are beneficial. Vitamin D is synthesized in skin exposed to UV radiation. A deficiency of this vitamin in the body can cause rickets or osteomalacia. Also, recent research suggests that sunlight can alter physical processes in ways that could enhance one's feeling of well-being.

Sunscreening agents exist naturally in the skin. These include melanin, carotenoids, urocanic acid, proteins and lipids. These natural sunscreens do not afford complete protection however, and for persons with very light skin they afford little protection at all.

Over the years, many means have been conceived of to mitigate the effects of UV exposure. In Middle Eastern countries people shield their skin with long robes, kaffiyehs and veils. This is not an acceptable solution for most people however.

Sunblock agents are commercially available to protect the skin from UV radiation. These agents scatter or reflect ultraviolet radiation. Examples include titanium dioxide and zinc oxide. However, compositions containing these agents are opaque, generally unattractive in color, and are viewed as unacceptable for usage on more than just the nose or tops of the ears. Furthermore, these agents are very susceptible to rub-off or wear-off resulting in little or no protection.

Another type of agent available is one which provides a "tan" without exposure to the sun. Such agents generally consist of a skin dye and in no way protect against harmful UV irradiation. These agents are applied to the skin wherever the appearance of a tan is desired. One example is dihydroxyacetone, which provides color through a reaction with specific amino acids in the stratum corneum. A drawback of this type of product is that it results in uneven coloration and a somewhat unnatural reddish-brown hue.

Related to these products are artificial tanning compounds which are taken orally. One example is canthaxanthin. These compounds apparently work by coloring the fat cells under the epidermal layer. Such products also result in uneven tanning and require continual maintenance doses. Again, these products provide no protection against harmful irradiation.

The most common agents for sun protection are sunscreens. These agents exert their effects through chemical means, i.e., they absorb ultraviolet radiation so that it cannot penetrate the skin. Sunscreens present the user with several problems. For example, they must be on the surface of the skin at the time of exposure to be effective. Sunscreens are preventative so one must anticipate being in the sun. To be most effective, sunscreens must be on the skin as a continuous uniform film. Delivering such a film to the surface of the skin is very difficult; maintaining the film over time is almost impossible. Sunscreens must remain on the surface of the skin during exposure. However, sunscreens are easily rubbed off or washed off by sweating or swimming and can also be lost by penetration into the skin. Sunscreening agents often cause irritation to the skin and eyes, primarily burning or stinging, respectively. Another problem with sunscreens is that the greater their efficacy, the more the tanning response is decreased.

Methods have been suggested for improving the look of skin after the UV-induced damage has occurred. Topical application of collagen as a moisturizing agent is one such method. Others involve injections of collagen or dimethylpolysiloxane. Yet another procedure entails the application of a chemical preparation to the skin to effect a "chemical peel".

Alternatively, methods have been suggested for repairing skin after UV-induced damage has occurred. One such method involves application of retinoic acid to the skin as disclosed in U.S. Pat. No. 4,603,146, Kligman, issued Jul. 29, 1986. None of these procedures have been proven to be fully effective and most involve extensive and costly treatment. Clearly, it would be far better to prevent the damage induced by UV-irradiation before it occurs. A photo-protecting agent which protects against both short-term and long-term UV-damage to the skin while, at the same time, allows for tanning of the skin in a safe, convenient manner would be most ideal.

Conjugated dienoic acids and their derivatives, in general, are known to be useful as quenchers for protecting the skin from harmful effects of UV exposure. For example, the use of a number of compounds, including 2,4-hexadien-1-ol, for controlling the chronic effects of prolonged exposure to sunlight is disclosed in U.S. Pat. No. 4,098,881, Majeti, issued Jul. 4, 1978. The use of sorbic acid or salts thereof in sunscreen formulations is also known. See e.g., U.S. Pat. No. 4,264,581, Kerkhof et al., issued Apr. 28, 1981.

Tocopherol (Vitamin E) has been disclosed for use as a photoprotector in topical compositions. See, e.g., U.S. Pat. No. 4,144,325, Voyt, issued Mar. 13, 1974. Tocopherol works to protect the skin from deleterious effects of UV-irradiation without interfering with the tanning response. However, cosmetic industry experience suggests that tocopherol may have stability problems, specifically oxidation problems. One frequently used approach to address these problems involves the formulation of compositions including esters of tocopherol, these esters generally being more stable than tocopherol itself. U.S. Pat. No. 4,248,861, Schutt, issued Feb. 3, 1981, discloses the use of tocopherol acetate, tocopherol succinate, tocopherol propionate, and tocopherol oleate for preventing deleterious effects to skin of solar radiation. U.S. Pat. No. 4,000,276, Hasunuma et al., issued Dec. 28, 1976, discloses a cosmetic composition comprising tocopherol orotate. Tocopherol benzoate, p-aminobenzoate, and p-nitro-benzoate have been disclosed for use in sunscreen compositions in European Patent Application 166,221, Tuominen, published Jan. 2, 1986. The linoleate, nicotinate, and 2-ethylhexanoate esters of tocopherol have been disclosed for use in cosmetic compositions in Japanese Laid-Open Application 61-143,331, published Dec. 14, 1984. Increased formulational stability, as provided by most tocopherol esters, unfortunately comes at the cost of decreased photoprotection efficacy. Clearly, a photo-protecting agent which works as well as tocopherol but which is not subject to stability problems would be most desirable.

The topical use of anti-inflammatory agents to alleviate erythema is known. Compositions containing steroidal anti inflammatories, non-steroidal anti-inflammatories, as well as "natural" anti-inflammatories, such as an extract of the plant *Aloe vera,* have been disclosed for such use. See e.g., U.S. Pat. No. 4,185,100, Rovee, issued Jan. 22, 1980 (hydrocortisone, dexamethasone, naproxen, ketoprofen, ibuprofen); U.S. Pat. No. 4,338,293, Holick, issued Jul. 5, 1982 (steroidal anti-inflammatories); Law, et al., *Br. J. Pharmac.,* 59(4), 591–597 (1977) (ibuprofen); Kaidbey, *J. Invest. Dermatology,* 66, 153–156 (1976) (indomethacin); and Gruber, et al., *Clinical Pharm. and Therapeut.,* 13(1), 109–113 (1971) (aspirin, fenoprofen). Short term application of anti-inflammatory agents prior to UV exposure to prevent erythema, as well as application after UV exposure to lessen UV-induced damage to skin, has been taught.

Hart, *Cosmetics and Toiletries,* 93(12), 28–30 (1978), discloses the utilization of low levels of chelating agents such as ethylenediaminetetraacetic acid (EDTA) in cosmetic formulations as preservatives. Particularly disclosed is the use of EDTA in sunscreen lotions and creams to prevent dark color formation from the reaction of p-aminobenzoic acid derivatives with iron. See also, Hart, *Cosmetics and Toiletries,* 98(4), 54–58 (1983). Japanese Patent Application 61-215,314 discloses a topical composition for protecting skin from UV-rays containing EDTA or a phosphoric acid or salt, 4-(1,1-dimethylethyl)4 '-methoxydibenzoylmethane and inorganic powders. The acids and their salts are added as preservatives. See also Japanese Patent Application 61-215,313, published Sep. 25, 1986, and U.S. Pat. No. 4,579,844, Rovee, issued Apr. 1, 1986. Wooley, et al., *Biochem. J.,* 169, 265–276 (1978), discloses the inhibition of skin collagenase utilizing EDTA, 1,10-phenanthroline, cysteine, dithiothreitol, or sodium aurothiemaleate.

It is an object of the present invention to provide a topical composition in a stable form, the use of which will prevent both acute (erythema) and chronic (photoaging) effects of exposure to the sun.

It is also an object of the present invention to provide a topical composition, a cleansing composition, and a method for preventing these deleterious effects of the sun without interfering with the tanning response.

It is further an object of the present invention to provide a photoprotection composition which penetrates into the skin and which is less susceptible to rub-off, wear-off or wash-off.

It is a still further object of the present invention to provide a photoprotection composition which can be applied to the skin in advance of UV exposure without significant loss of efficacy.

SUMMARY OF THE INVENTION

The present invention relates to a composition useful for topical application comprising a safe and photoprotectively effective amount of a specifically selected chelating agent and a safe and effective amount of a topical carrier.

The present invention also relates to a composition useful for topical application comprising a safe and photoprotectively effective amount of a specifically selected chelating agent in combination with a safe and effective amount of a topical carrier and any or all of the following: a safe and photoprotectively effective amount of a sunscreening agent, a safe and photoprotectively effective amount of an anti-inflammatory agent, and a safe and photoprotectively effective amount of tocopherol sorbate.

The present invention further relates to a method of inhibiting the deleterious effects of ultraviolet light exposure to skin comprising applying a safe and photoprotectively effective amount of a specifically selected chelating agent to the skin in conjunction with exposing the skin to ultraviolet light.

The present invention also relates to a method of inhibiting the deleterious effects of ultraviolet light exposure to skin comprising applying a safe and photoprotectively effective amount of a specifically selected chelating agent in combination with any or all of the following: a safe and photoprotectively effective amount of a sunscreening agent, a safe and photoprotectively amount of an anti-inflammatory agent, and a safe and photoprotectively effective amount of tocopherol sorbate, to the skin in conjunction with exposing the skin to ultraviolet light.

DETAILED DESCRIPTION OF THE INVENTION

Active Agent

It is well-known that ultraviolet light induces inflammation of the skin and harmful photochemical reactions therein. During exposure and as repair of the UV damage takes place, super-oxide ($O_2^-$) radicals are formed in the skin. UV irradiation also causes some microvascular damage in the skin. Kligman et al., *Photoderm.*, 3, 215–227 (1986). This leads to local hemorrhage and "leakage" of blood cells into the dermis. Iron from the hemoglobin accumulates in the extra-cellular matrix of the tissue as $Fe^{+2}$ and $Fe^{+3}$. It is known that iron catalytically participates in the conversion of superoxide radicals to hydroxyl radicals, a species which is known to be very damaging to tissue. (See Davies, *J. Biol. Chem.*, Vol. 262, No 20 (1987), pp. 9895–9901). Another process which is damaging to tissue is membrane lipid peroxidation, which is also accelerated by iron. (See Holliwell and Gutteridge, *Free Radicals in Biology and Medicine*, Claredon Press, Oxford, England (1985), p. 147). It is believed that this damage results in premature aging of the skin. The deposited iron may also be taken up by viable skin cells. This can result in iron-catalyzed DNA damage within the cells which may ultimately cause the formation of tumors or abnormal matrix components in the skin. It is also known that other metal ions such as $Cu^{+1}$ or $Cu^{+2}$ can participate catalylically in generation of oxygen radicals and that such ions may also result in skin damage.

Black, *Photochem. Photobiol.*, 46(2), 213–221 (1987), speculates, based on circumstantial evidence, that free radicals may cause at least some UV-induced skin damage. The effect of systemically or intraperitoneally administered antioxidants on peroxide formation is discussed.

Braughler, et al., *J. Biol. Chem.*, 261(22), 10282–10289 (1986), discusses iron-initiated lipid peroxidation reactions in the context of brain synoptosomes. It is shown that the use of a chelator, EDTA, will prevent the reactions from starting.

Nunez et al., *J. Biol. Chem.*, 258(2), 1146–1151 (1983), discusses the cellular mechanism by which iron is released by reticulocytes. It was found that iron (II) chelators (e.g., phenanthroline, dipyridyl), but not iron (III) chelators, were useful in the study of this mechanism.

deMello Filho, et al., *Biochem. et Biophys. Acta*, 847, 82–89 (1985), describes cell culture work which suggests that the inhibition of the iron-initiated peroxidation reaction by phenanthroline may prevent cellular damage caused by inflammation.

Morgan, *Biochem. Biophys. Acta*, 733(1), 39–50 (1983), discusses the mechanism by which certain iron chelators inhibit cellular iron uptake after release from transferrin while it is still in the membrane fraction of the cells.

It has now been found that certain metal chelators, which are able to "tie-up" free iron, thus impairing its catalytic activity, protect the skin from aging effects caused by UV exposure.

Not all chelating agents are useful in the present invention. Chelating agents which may be used herein must be safe for topical application and exhibit a photoprotective effect. By "safe" is meant chelating agents which may be used topically, at typical usage levels for extended periods of time, without causing any significant adverse skin reactions or other side effects. Whether a chelating agent exhibits a photoprotective effect can be determined using either of the following test methods.

Test Method I

In Vitro Solution Radical Assay

One method for determining whether any particular chelating agent is useful in the present invention is the in vitro solution radical assay. This assay may be used to identify chelators that have the ability to scavenge or to inhibit hydroxyl radical formation. The assay is based on the OH. oxidation of methional to ethylene. The efficacy of any given chelator is determined from its ability to inhibit ethylene formation.

More specifically, the method (based on Zigler et al., *Arch Biochem. Biophys.*, 241(1), 163–172 (1985) and Tauber et al., *J. Clin. Invest.*, 60, 374–379 (1977)) is carried out as follows. The following materials are added to a one dram vial: 200 ul phosphate buffered saline (PBS), 100 ul of 1.4 mM hypoxanthine in PBS, 100 ul of 1.0 mM $FeSO_4$ in PBS, 100 ul of 3.0 mM EDTA in PBS, molecule to be tested, 100 ul of 3.5 mM methional in PBS, 100 ul xanthine oxidase (0.1 unit of enzyme/ml). The reaction vial is then capped with Self-Seal Septa Assembled in Vial Cap (Waters Associates, Cat. #73010), gently mixed on a Vortex Genie, and incubated at 37° C. for 20 min. in an Aquatherm Water Bath Shaker (New Brunswick Scientific). At this time the reaction is stopped by placing all samples at −10° C. in a Lauda RM-20 constant temperature bath. One 500 ul aliquot (Pressure lock syringe, Precision Sampling Corporation) is then injected into a Gas Chromatograph (HP0- 5880 A) fitted with a chromosorb 102 column (10 ft× ⅛" O.D.) at an oven temperature of 35° C. using helium as the carrier gas at 30 ml/min. Triplicate preparations are run for each scavenger tested; the control contains no enzyme (no ethylene should be produced). Calibration of the Gas Chromatograph is done by injecting various volumes of ethylene gas (Supelco #2-2572) of known concentration and correlating the amount injected with total peak area. An ethylene standard is run for each set of experiments.

The % inhibition of hydroxyl radical formation is determined by the following method: First, all peak areas from the chromatograms are converted into picomoles (p moles) of ethylene using a calibration curve for ethylene. Then, according to the equation:

$$\frac{\text{pmoles } C_2H_4 \text{ w/o scavenger} - \text{pmoles } C_2H_4 \text{ with scavenger} \times 100}{\text{pmoles } C_2H_4 \text{ w/o scavenger}} = \% \text{ Inhibition.}$$

Chelating agents which exhibit at least about a 50% inhibition of iron-catalyzed hydroxyl radical formation in this assay are useful in the present invention.

Test Method II

In Vivo Mouse Skin Wrinkling Test

A second test useful for screening chelators for photoprotective capability is the in vivo mouse skin wrinkling test which measures premature wrinkling inhibition, described in D. L. Bissett, D. P. Hannon & T. V. Orr, "An Animal Model of Solar-Aged Skin: Histological, Physical, and Visible Changes in UV-Irradiated Hairless Mouse Skin", *Photochem. Photobiol.*, Vol. 46 (1987), pp. 367–378, which is hereby incorporated by reference.

The test is used to determine the photoprotective efficacy of topically applied materials against UVB-induced photoaging. The work is done with Skh:HR-1 hairless mice.

A chelator to be screened is dissolved in a liquid vehicle; preferred vehicles are ethanol, isopropanol, water, propylene glycol, or mixtures thereof. The test material solution is 5% (w/v) chelator (or saturated with chelator if the chelator is not soluble at 5% in any reasonable vehicle).

Test material solutions are applied topically to the dorsal skin of the mouse. A control group of mice receives topical application of the same vehicle as is in the test material solution (without the chelating agent). Test material solution or control vehicle is applied to the skin of each mouse at an application rate of approximately 2 $\mu l/cm^2$. Topical treatments are done three times each week.

A bank of four 4-foot fluorescent UVB lamps (Westinghouse FS-40 sunlamps) is used. The energy output of the lamps is measured with an International Light (Newburyport, Mass.) model 700 A research radiometer. Mice are irradiated with 30 $mJ/cm^2$ of UVB per exposure. Irradiations are done two hours after each topical application of the test material solution or vehicle.

Once each week, mice are observed for skin wrinkling (see Bissett, et al., *Photochem. Photobiol.*, 46, 367–378, 1987). Wrinkles are graded on a 0–3 scale as described in this reference. The test is continued until the skin wrinkle grade of the control group is at least about 2.0; generally the test requires about 20 weeks to complete.

Chelating agents which exhibit at least about a 20% reduction in skin wrinkle grade in Test Method II are useful in the present invention. Preferred chelating agents exhibit at least about a 30% reduction in skin wrinkle grade; more preferred chelating agents exhibit at least about a 60% reduction in skin wrinkle grade; most preferred chelating agents exhibit at least about a 90% reduction in skin wrinkle grade.

A composition of the present invention may be tested using Test Method II to determine its effective dosage levels and appropriate formulations and methods of application. For example, if a chelator shown to be effective using Test Method I is shown in Test Method II to be a relatively ineffective photoprotective agent due to its inablility to penetrate the skin, it may be formulated with a skin penetration enhancer to enhance its efficacy.

The chelating agents useful in the present invention may be classified according to their donor groups; see Martell, A. E., "The Design and Synthesis of Chelating Agents", *Development of Iron Chelators for Clinical Use*, Martell, Anderson and Badman, eds., Elsevier North Holland, Inc., New York, N.Y. (1981), pp. 67–104, which is hereby incorporated by reference. Because some chelating agents have more than one type of donor group, they may fall into more than one of the classes defined in Martell.

Preferred classes containing chelating agents useful in the present invention are aromatic amine, carbonyl, oximate, amine, carboxylate, alkoxide, enolate, phenoxide, catecholate, hydroxy acid, hydroxamate, ketoenolate, mercaptide, hydroxy aromatic amine, and aromatic hydroxy acid. More preferred classes are aromatic amine, carbonyl, oximate, enolate, phenoxide, catecholate and hydroxylate; especially preferred are aromatic amine, carbonyl, oximate and enolate.

Preferred chelating agents useful in the present invention which fall within the class of aromatic amines include the following: 2,2'-dipyridylamine; 1,10-phenanthroline {o-phenanthroline}; di-2-pyridyl ketone; 2,3-bis(2-pyridyl) pyrazine; 2,3-bis(2-pyridyl)-5,6-dihydropyrazine; 1,1'-carbonyldiimidazole; 2,4-bis(5,6-diphenyl-1,2,4-triazine-3-yl)pyridine; 2,4,6-tri(2-pyridyl)-1,3,5-triazine; 4,4'-dimethyl-2,2'-dipyridyl; 2,2'-biquinoline; di-2-pyridyl glyoxal {2,2'-pyridil}; 2-(2-pyridyl)benzimidazole; 2,2'-bipyrazine; 3-(2-pyridyl) 5,6-diphenyl-1,2,4-triazine; 3-(4-phenyl-2-pyridyl)-5-phenyl- 1,2,4-triazine; 3-(4-phenyl-2-pyridyl)-5,6-diphenyl-1,2,4-triazine; 2,3,5,6-tetrakis-( 2'-pyridyl)-pyrazine; 2,6-pyridinedicarboxylic acid; 2,4,5-trihydroxypyrimidine; phenyl 2-pyridyl ketoxime; 3-amino-5,6-dimethyl- 1,2,4-triazine; 6-hydroxy-2-phenyl-3(2H)-pyridazinone; 2,4-pteridinediol {lumazine}; 2,2'-dipyridyl; and 2,3-dihydroxypyridine. Other preferred chelating agents are analogs, homologs and isomers of the above aromatic amines which exhibit at least about 50% inhibition of iron-catalyzed hydroxyl radical formation in the in vitro solution radical assay or at least about a 20% reduction in skin wrinkle grade in the in vivo mouse skin wrinkling test.

Preferred chelating agents useful in the present invention which fall within the class of carbonyls include the following: di-2-pyridyl ketone; 1,1'-carbonyldiimidazole and 2,2'-pyridil. Other preferred chelating agents are analogs, homologs and isomers of the above carbonyls which exhibit at least about 50% inhibition of iron-catalyzed hydroxyl radical formation in the in vitro solution radical assay or at least about a 20% reduction in skin wrinkle grade in the in vivo mouse skin wrinkling test.

Preferred chelating agents useful in the present invention which fall within the class of oximates include the following: 2-furildioxime; phenyl 2-pyridyl ketoxime; and 1,2-cyclohexanedione dioxime. Other preferred chelating agents are analogs, homologs and isomers of the above oximates which exhibit at least about 50% inhibition of iron-catalyzed hydroxyl radical formation in the in vitro solution radical assay or at least about a 20% reduction in skin wrinkle grade in the in vivo mouse skin wrinkling test.

Preferred chelating agents useful in the present invention which fall within the class of amines include the following: ethylenediamine-N,N-bis-(2-hydroxyphenylacetic acid) dimethyl ester; diethyldithiocarbamic acid; 1-pyrrolidinecarbodithioic acid; and 3-amino-5,6-dimethyl-1,2,4-triazine. Other preferred chelating agents are analogs, homologs and isomers of the above amines which exhibit at least about 50% inhibition of iron-catalyzed hydroxyl radical formation in the in vitro solution radical assay or at least about a 20% reduction in skin wrinkle grade in the in vivo mouse skin wrinkling test.

Preferred chelating agents useful in the present invention which fall within the class of carboxylates include the following: 2,3-dihydroxybenzoic acid; 3-hydroxy- 5-(hydroxymethyl)-2-methyl- 4-pyridine-carboxylic acid {pyridoxic acid}; ethylenediamine-N,N-bis-(2-hydroxyphenylacetic acid) dimethyl ester; and 2,6-pyridinedicarboxylic acid. Other preferred chelating agents are analogs, homologs and isomers of the above carboxylates which exhibit at least about 50% inhibition of iron-catalyzed hydroxyl radical formation in the in vitro solution radical assay or at least about a 20% reduction in skin wrinkle grade in the in vivo mouse skin wrinkling test.

Preferred chelating agents useful in the present invention which fall within the class of alkoxides include the following: 5-hydroxy-2-(hydroxymethyl)-4H-pyran-4-one {kojic acid} and pyridoxic acid. Other preferred chelating agents are analogs, homologs and isomers of the above alkoxides which exhibit at least about 50% inhibition of iron-catalyzed hydroxyl radical formation in the in vitro solution radical assay or at least about a 20% reduction in skin wrinkle grade in the in vivo mouse skin wrinkling test.

Preferred chelating agents useful in the present invention which fall within the class of enolates include the following: 1,2-dimethyl-3-hydroxypyrid-4-one; 3-hydroxy- 2-methyl-4-pyrone; kojic acid; 1-hydroxy-4-methyl-6-( 2,4,4-trimethylpentyl)-2(1H)-pyridone {piroctone olamine—Octopirox}; and 6-cyclohexyl- 1-hydroxy-4-methyl-2(1H)-pyridinone {Ciclopirox}. Other preferred chelating agents are analogs, homologs and isomers of the above enolates which exhibit at least about 50% inhibition of iron-catalyzed hydroxyl radical formation in the in vitro solution radical assay or at least about a 20% reduction in skin wrinkle grade in the in vivo mouse skin wrinkling test.

Preferred chelating agents useful in the present invention which fall within the class of phenoxides include the following: Octopirox; 6-hydroxy-2-phenyl-3( 2H)-pyridazinone; Ciclopirox; 2,3-dihydroxybenzoic acid; 4,5-dihydroxy- 1,3-benzene-disulfonic acid {Tiron}; ethylenediamine-N,N-bis-(2-hydroxyphenylacetic acid) dimethyl ester; pyridoxic acid; 2,3-dihydroxypyridine; 2,4, 5-trihydroxypyrimidine; and 2,3-dihydroxynaphthalene. Other preferred chelating agents are analogs, homologs and isomers of the above phenoxides which exhibit at least about 50% inhibition of iron-catalyzed hydroxyl radical formation in the in vitro solution radical assay or at least about a 20% reduction in skin wrinkle grade in the in vivo mouse skin wrinkling test.

Preferred chelating agents useful in the present invention which fall within the class of catecholates include the following: 2,3-dihydroxynaphthalene; 2,4,5-trihydroxypyrimidine; kojic acid; 2,3-dihydroxypyridine; 3-hydroxy-2-methyl- 4-pyrone; Tiron; 2,3-dihydroxybenzoic acid; 4-(2-amino-1-hydroxyethyl)- 1,2-benzenediol; Ciclopirox; and Octopirox. Other preferred chelating agents are analogs, homologs and isomers of the above catecholates which exhibit at least about 50% inhibition of iron-catalyzed hydroxyl radical formation in the in vitro solution radical assay or at least about a 20% reduction in skin wrinkle grade in the in vivo mouse skin wrinkling test.

Preferred chelating agents useful in the present invention which fall within the class of hydroxy acids include the following: 2,3-dihydroxybenzoic acid; and pyridoxic acid. Other preferred chelating agents are analogs, homologs and isomers of the above hydroxy acids which exhibit at least about 50% inhibition of iron-catalyzed hydroxyl radical formation in the in vitro solution radical assay or at least about a 20% reduction in skin wrinkle grade in the in vivo mouse skin wrinkling test.

Preferred chelating agents useful in the present invention which fall within the class of hydroxamates include the following: N-benzoyl -N-phenyl-hydroxylamine; desferrioxamine B {Desferal}; Ciclopirox; and Octopirox. Other preferred chelating agents are analogs, homologs and isomers of the above hydroxamates which exhibit at least about 50% inhibition of iron-catalyzed hydroxyl radical formation in the in vitro solution radical assay or at least about a 20% reduction in skin wrinkle grade in the in vivo mouse skin wrinkling test.

Preferred chelating agents useful in the present invention which fall within the class of ketoenolates include the following: kojic acid. Other preferred chelating agents are analogs, homologs and isomers of the above ketoenolates which exhibit at least about 50% inhibition of iron-catalyzed hydroxyl radical formation in the in vitro solution radical assay or at least about a 20% reduction in skin wrinkle grade in the in vivo mouse skin wrinkling test.

Preferred chelating agents useful in the present invention which fall within the class of mercaptides include the following: diethyldithiocarbamic acid; and 1-pyrrolidinecarbodithioic acid. Other preferred chelating agents are analogs, homologs and isomers of the above mercaptides which exhibit at least about 50% inhibition of iron-catalyzed hydroxyl radical formation in the in vitro solution radical assay or at least about a 20% reduction in skin wrinkle grade in the in vivo mouse skin wrinkling test.

Preferred chelating agents useful in the present invention which fall within the class of hydroxy aromatic amines include the following: 5,7-dichloro-8-hydroxyquinoline. Other preferred chelating agents are analogs, homologs and isomers of the above hydroxy aromatic amines which exhibit at least about 50% inhibition of iron-catalyzed hydroxyl radical formation in the in vitro solution radical assay or at least about a 20% reduction in skin wrinkle grade in the in vivo mouse skin wrinkling test.

Preferred chelating agents useful in the present invention which fall within the class of aromatic hydroxy acids include the following: 2,3-dihydroxybenzoic acid; pyridoxic acid; and 2,6-pyridinedicarboxylic acid. Other preferred chelating agents are analogs, homologs and isomers of the above aromatic hydroxy acids which exhibit at least about 50% inhibition of iron-catalyzed hydroxyl radical formation in the in vitro solution radical assay or at least about a 20% reduction in skin wrinkle grade in the in vivo mouse skin wrinkling test.

More preferred chelating agents for use in the compositions and methods of the present invention include the following: 2,2'-dipyridylamine; o-phenanthroline; di-2-pyridyl ketone; 2-furildioxime; 2,3-bis(2-pyridyl) pyrazine; Octopirox; 2,3-dihydroxybenzoic acid; ethylenediamine-N, N-bis-(2-hydroxyphenylacetic acid), dimethyl ester; 1,1'-carbonyldiimidazole; 1,2-dimethyl-3-hydroxypyrid-4-one; 2,4,6-tri( 2-pyridyl)-1,3,5-triazine; 1-pyrrolidinecarbodithioic acid; diethyldithiocarbamic acid; Ciclopirox; 2,2'-dipyridyl; 1,2-cyclohexanedione dioxime; 3-hydroxy-2-methyl-4-pyrone; 2,3-bis(2-pyridyl)-5,6-dihydropyrazine; 3-(4-phenyl-2-pyridyl)-5-phenyl- 1,2,4-triazine; kojic acid; 2,3-dihydroxypyridine; 2,2'-biquinoline; 2,2 '-bipyrazine; 3-(2-pyridyl)-5,6-diphenyl- 1,2,4-triazine; 4-(2-amino-1-hydroxyethyl)- 1,2-benzenediol; and 4,4'-dimethyl-2,2'-dipyridyl.

Still more preferred chelating agents for use in the compositions and methods of the present invention including the following: 2,2 '-dipyridylamine; o-phenanthroline, di-2-pyridyl ketone; 2-furildioxime; 2,3-bis(2-pyridyl) pyrazine; Octopirox; 2,3-dihydroxybenzoic acid; ethylenediamine-N, N-bis-( 2-hydroxyphenylacetic acid), dimethyl ester; 1,1'-carbonyldiimidazole; 1,2-dimethyl-3-hydroxypyrid-4-one; 2,4,6-tri( 2-pyridyl)-1,3,5-triazine; 1-pyrrolidinecarbodithioic acid; diethyldithiocarbamic acid; and Ciclopirox.

More preferred still chelating agents for use in the compositions and methods of the present invention including the following: 2,2'-dipyridylamine; o-phenanthroline, di-2-pyridyl ketone; 2-furildioxime; 2,3-bis(2-pyridyl) pyrazine; Octopirox; 2,3-dihydroxybenzoic acid; and ethylenediamine-N,N-bis-( 2-hydroxyphenylacetic acid), dimethyl ester.

Most preferred chelating agents for use in the compositions and methods of the present invention include the following: 2,2'-dipyridylamine; o-phenanthroline; di-2-pyridyl ketone; and 2-furildioxime.

The preferred chelating agents listed hereinabove are generally commercially available from one or more of the following suppliers: Aldrich Chemical Company, Milwaukee, Wis.; G.F.S. Chemicals, Columbus, Ohio; Dojindo Laboratories, Kumamoto, Japan; Sigma Chemical Company, St. Louis, Mo.; Ciba-Geigy, Summit, N.J.; Strem Chemicals, Newburyport, Mass.; and American Hoechst Corp., Summerville, N.J. A method for synthesizing 1,2-dimethyl-3-hydroxypyrid-4-one is disclosed in Kontoghiorghes, G. J., "L1—1,2-dimethyl- 3-hydroxypyrid-4-one", *Drugs of the Future*, Vol. 13, No. 5 (1988), pp. 413–415, which is hereby incorporated by reference.

A safe and photoprotectively effective amount of a chelating agent is used in the compositions of the present invention. Typically, this is from about 1% to about 10%, preferably from about 2% to about 5%, of the composition.

It is important to note that the chelating agent is predominantly a non-sunscreen photoprotecting agent. A sunscreen works on the surface of the skin to absorb UV radiation so that the harmful rays never enter the skin. The chelating agent works in the skin to prevent damaging reactions in the skin. Because the chelating agent penetrates the skin to work, rub-off, wear-off or wash-off of the active, which lessen efficacy for sunscreens considerably, are essentially irrelevant with the present invention. Furthermore, though critical with a sunscreen, it is not necessary to keep an even coating of the active of the present invention on the skin for the entire exposure period. The chelating agent can be applied to the skin up to four hours or longer prior to UV exposure. The chelating agent protects against both acute effects of UV exposure, e.g., sunburn, and chronic effects, of UV exposure, e.g., premature aging of the skin.

Carriers

In addition to the active agent, the compositions of the present invention contain a safe and effective amount of an acceptable carrier. The term "acceptable topical carrier" encompasses both pharmaceutically-acceptable carriers and cosmetically-acceptable carriers, and it encompasses substantially nonirritating compatible components (either taken alone or in mixtures) which are suitable for delivering the active component to the skin. The term "compatible", as used herein, means that the components of the carrier must be capable of being commingled with the chelating agent, and with each other, in a manner such that there is no interaction which would substantially reduce the efficacy of the composition during use for protecting the skin from the effects of UV radiation. These carriers must, of course, be of sufficiently high purity and sufficiently low toxicity to render them suitable for chronic topical administration to the skin of humans or lower animals. The term "safe and effective amount" of carrier means an amount sufficient to deliver the chelating agent to the skin but not so much as to cause any side effects or skin reactions, generally from about 50% to about 99%, preferably from about 90% to about 98%, of the composition.

Variations in formulation of these carriers will result in a wide variety of products which fall within the scope of the present invention. These product types can be divided into two classes: pharmaceutical/cosmetic compositions and cleaning compositions.

Pharmaceutical/Cosmetic Compositions

The pharmaceutical/cosmetic compositions of the present invention may be made into a wide variety of product types. These include, for example, lotions, creams, beach oils, gels, sticks, sprays, ointments, pastes, mousses and cosmetics. These product types may comprise either of two basic types of carrier systems, i.e., solutions and emulsions.

The pharmaceutical/cosmetic compositions of the present invention formulated as solutions typically include a pharmaceutically- or cosmetically-acceptable organic solvent. The terms "pharmaceutically-acceptable organic solvent" and "cosmetically-acceptable organic solvent" refer to an organic solvent which, in addition to being capable of having dispersed or dissolved therein the chelating agent, also possesses acceptable safety (e.g. irritation and sensitization characteristics), as well as good aesthetic properties (e.g., does not feel greasy or tacky). The most typical example of such a solvent is water. Examples of other suitable organic solvents include: propylene glycol, polyethylene glycol (200–600), polypropylene glycol (425–2025), glycerol, 1,2,4-butanetriol, sorbitol esters, 1,2, 6-hexanetriol, ethanol, isopropanol, butanediol, and mixtures thereof. These solutions contain from about 1% to about 20%, preferably from about 2% to about 10%, of the chelating agent, and from about 80% to about 99%, preferably from about 90% to about 98%, of an acceptable organic solvent.

If the pharmaceutical/cosmetic compositions of the present invention are formulated as an aerosol and applied to the skin as a spray-on, a propellant is added to a solution composition. Examples of propellants useful herein include the chlorinated, fluorinated and chloro-fluorinated lower molecular weight hydrocarbons. Other propellants useful in the present invention include lower molecular weight hydrocarbon mixtures (e.g., the mixture of butane, isobutane and propane known commercially as Propellant A46, made by Phillips Chemical Co., a subsidiary of Phillips Petroleum Company), ethers and halohydrocarbons such as dimethyl ether or dichlorodifluoromethane alone or mixtures thereof with dichlorotetrafluoroethane. Mixtures of hydrocarbon and halohydrocarbon propellants and nitrous oxide may also be used. Nitrogen and carbon dioxide can also be used as propellant gases. They are used at a level sufficient to expel the contents of the container. A more complete disclosure of propellants useful herein can be found in Sagarin, *Cosmetics Science and Technology*, 2nd Edition, Vol. 2, pp. 443–465 (1972), incorporated herein by reference.

Alternatively, emollients may comprise the carrier system of the present invention formulated as a solution. An example of a composition formulated in this way would be a beach oil product. Such compositions contain from about 1% to about 20% of the chelating agent and from about 2% to about 50% of a pharmaceutically/cosmetically-acceptable emollient.

As used herein, "emollients" refer to materials used for the prevention or relief of dryness, as well as for the protection of the skin. A wide variety of suitable emollients are known and may be used herein. Sagatin, *Cosmetics, Science and Technology*, 2nd Edition, Vol. 1, pp. 32–43 (1972), incorporated herein by reference, contains numerous examples of suitable materials.

A lotion can be made from a solution carrier system. Lotions typically comprise from about 1% to about 20%, preferably from about 2% to about 10%, of the chelating agent; from about 1% to about 20%, preferably from about 5% to about 10%, of an emollient; and from about 50% to about 90%, preferably from about 60% to about 80%, water. Another type of product that may be formulated from a solution carrier system is a cream. A cream of the present invention would comprise from about 1% to about 20%, preferably from about 2% to about 10%, of the chelating agent; from about 5% to about 50%, preferably from about 10% to about 20%, of an emollient, and from about 45% to about 85%, preferably from about 50% to about 75%, water.

Yet another type of product that may be formulated from a solution carrier system is an ointment. An ointment may comprise a simple base of animal or vegetable oils or semi-solid hydrocarbons (oleaginous). Ointments may also comprise absorption ointment bases which absorb water to form emulsions. Examples of such ointment bases include, anhydrous lanolin and hydrophilic petrolatum. Emulsion ointment bases may be oil-in-water or water-in-oil emulsions. Ointment carriers may also be water soluble. Examples of such ointment carriers include glycol ethers, propylene glycols, polyoxyl stearates, and polysorbates. An ointment may also comprise from about 2% to about 10% of an emollient plus from about 0.1% to about 2% of a thickening agent. Examples of suitable thickening agents include: cellulose derivatives (e.g., methyl cellulose and hydroxy propylmethyl cellulose), synthetic high molecular weight polymers (e.g., carboxyvinyl polymer and polyvinyl alcohol), plant hydrocolloids (e.g., karaya gum and tragacanth gum), clay thickeners (e.g., colloidal magnesium aliminum silicate and bentonite), and carboxyvinyl polymers (Carbopols®—sold by B. F. Goodrich Company, such polymers are described in detail in U.S. Pat. No. 2,798,053, Brown, issued Jul. 2, 1975, incorporated herein by reference). A more complete disclosure of thickening agents useful herein can be found in Segatin, *Cosmetics, Science and Technology*, 2nd Edition, Vol. 1, pp. 72–73 (1972), incorporated herein by reference.

If the carrier is formulated as an emulsion, from about 1% to about 10%, preferably from about 2% to about 5%, of the carrier system comprises an emulsifier. Emulsifiers may be nonionic, anionic or cationic. Suitable emulsifiers are disclosed in, for example, U.S. Pat. No. 3,755,560, issued Aug. 28, 1973, Dickert et al,; U.S. Pat. No. 4,421,769, issued Dec. 20, 1983, Dixon et al.; and McCutcheon's *Detergents and Emulsifiers*, North American Edition, pages 317–324 (1986); the disclosures of which are incorporated herein by reference. Preferred emulsifiers are anionic or nonionic, although the other types may also be used.

Single emulsion skin care preparations, such as lotions and creams, of the oil-in-water type and water-in-oil type are well-known in the cosmetic art and are useful in the present invention. Multiphase emulsion compositions, such as the water-in-oil-in-water type, as disclosed in U.S. Pat. No. 4,254,105, Fakuda et al., issued Mar. 3, 1981, herein incorporated by reference, are also useful in the present invention. In general, such single or multiphase emulsions contain water, emollients and emulsifiers as essential ingredients.

Triple emulsion carrier systems comprising an oil-in-water-in-silicone fluid emulsion composition as disclosed in U.S. patent application Ser. No. 022,876, Figueroa, et al., filed Mar. 6, 1987, herein incorporated by reference, are also useful in the present invention. This triple emulsion carrier system can be combined with from about 1% to about 20%, preferably from about 2% to about 10%, of the chelating agent to yield the pharmaceutical/cosmetic composition of the present invention.

Another emulsion carrier system useful in the pharmaceutical/cosmetic compositions of the present invention is a microemulsion carrier system. Such a system comprises from about 9% to about 15% squalane; from about 25% to about 40% silicone oil; from about 8% to about 20% of a fatty alcohol; from about 15% to about 30% of polyoxyethylene sorbitan mono-fatty acid (commercially available under the trade name Tweens) or other nonionics; and from about 7% to about 20% water. This carrier system is combined with from about 2% to about 10% of the chelating agent.

Lotions and creams can be formulated as emulsions as well as solutions. Typically such lotions comprise from about 1% to about 20%, preferably from about 2% to about 10%, of the chelating agent; from about 1% to about 20%, preferably from about 5% to about 10%, of an emollient; from about 25% to about 75%, preferably from about 45% to about 95%, water; and from about 1% to about 10%, preferably from about 2% to about 5%, of an emulsifier. Such creams would typically comprise from about 1% to about 20%, preferably from about 2% to about 10%, of the chelating agent; from about 1% to about 20%, preferably from about 5% to about 10%, of an emollient; from about 20% to about 80%, preferably from about 30% to about 70%, water; and from about 1% to about 10%, preferably from about 2% to about 5%, of an emulsifier.

If the pharmaceutical/cosmetic compositions of the present invention are formulated as a gel or a cosmetic stick, a suitable amount of a thickening agent, as disclosed supra, is added to a cream or lotion formulation.

The pharmaceutical/cosmetic compositions of the present invention may also be formulated as makeup products such as foundations, or lipsticks. Foundations are solution or lotion-based with appropriate amounts of thickeners, pigments and fragrance. Lipsticks are composed essentially of an oil-wax base stiff enough to form a stick, with pigmentation dispersed therein.

The topical pharmaceutical/cosmetic compositions of the present invention may contain, in addition to the aforementioned components, a wide variety of additional oil-soluble materials and/or water-soluble materials conventionally used in topical compositions, at their art-established levels.

Among the optional oil-soluble materials are nonvolatile silicone fluids, such as polydimethyl siloxanes with viscosities ranging from about 10 to about 100,000 centistokes at 25° C. These siloxanes are useful to enhance skin feel and are available from Dow Corning Corporation as the Dow Corning 200 series. These optional oil-soluble materials may comprise up to about 20% of the total composition, preferably up to about 10%.

Various water-soluble materials may also be present in the compositions of this invention. These include humectants, such as glycerol, sorbitol, propylene glycol, alkoxylated glucose and hexanetriol, ethyl cellulose, polyvinyl alcohol, carboxymethyl cellulose, vegetable gums and clays such as Veegum® (magnesium aluminum silicate, R. T. Vanderbilt, Inc.); proteins and polypeptides; preservatives such as the methyl, ethyl, propyl and butyl esters of hydroxybenzoic acid (Parabens—Mallinckrodt Chemical Corporation), EDTA, methylisothiazolinone and imidazolidinyl ureas (Germall 115—Sutton Laboratories); and an alkaline agent such as sodium hydroxide or potassium hydroxide to neutralize, if desired, part of the fatty acids or thickener which may be present. In addition, the topical compositions herein can contain conventional cosmetic adjuvants, such as dyes, opacifiers (e.g., titanium dioxide), pigments and perfumes.

The pharmaceutical/cosmetic compositions of the present invention may also include a safe and effective amount of a penetration enhancing agent. By "safe and effective amount" is meant an amount sufficient to enhance penetration of the chelating agent into the skin but not so much as to cause any side effects or skin reactions, generally from about 1% to about 5% of the composition. Examples of useful penetration enhancers, among others, are disclosed in U.S. Pat. No. 4,537,776, Cooper, issued Aug. 27, 1985; U.S. Pat. No. 4,552,872, Cooper et al., issued Nov. 12, 1985; U.S. Pat. No. 4,557,934, Cooper, issued Dec. 10, 1985; U.S. Pat. No. 4,130,667, Smith, issued Dec. 19, 1978; U.S. Pat. No. 3,989,816, Rhaadhyaksha, issued Nov. 2, 1976; U.S. Pat. No. 4,017,641, DiGiulio, issued Apr. 12, 1977; and European Patent Application 0043738, Cooper et al., published Jan. 13, 1982. U.S. Pat. No. 4,537,776 teaches a penetration-enhancing vehicle consisting essentially of a) N-(2-hydroxyethyl) pyrrolidone and b) a cell envelope disordering compound selected from methyl laurate, oleic acid, oleyl alcohol, monoolein, myristyl alcohol, and mixtures thereof, wherein component (a) and (b) are present in a ratio of (a):(b) of about 1:5 to about 500:1 by weight. U.S. Pat. No. 4,557,934 teaches a pharmaceutical composition comprising the penetration enhancing agent 1-dodecylazacycloheptan-2-one, and a penetration enhancing diol or cycloketo compound selected from the group consisting of: 1,2-propanediol, 1,3-propanediol, 1,2-butanediol, pyrrolidone; 1-(2-hydroxyethyl)-azacyclopentan-2-one, and mixtures thereof. U.S. Pat. No. 4,130,667 describes a penetration enhancer comprising:

(a) at least about 0.1% by weight of a sugar ester selected from sucrose monooctanoate, sucrose monodecanoate, sucrose monolaurate, sucrose monomyristate, sucrose monopalmitate, sucrose monostearate, sucrose monooleate, and sucrose dioleate; and (b) at least about 0.1% by weight of a phosphine oxide compound selected from octyldimethyl phosphine oxide, nonyl dimethyl phosphine oxide, decyl dimethyl phosphine oxide, undecyl dimethyl phosphine oxide, dodecyl dimethyl phosphine oxide, 2-hydroxydecyl dimethyl phosphine oxide, 2-hydroxy undecyl dimethyl phosphine oxide, and 2-hydroxy dodecyl dimethyl phosphine oxide.

Sulfoxides may be used in some executions in place of the phosphine oxide.

Other conventional skin care product additives may also be included in the compositions of the present invention. For example, collagen, hyaluronic acid, elastin, hydrolysates, primrose oil, jojoba oil, epidermal growth factor, soybean saponins, mucopolysaccharides, and mixtures thereof may be used.

Various vitamins may also be included in the compositions of the present invention. For example, Vitamin A, and derivatives thereof, Vitamin $B_2$, biotin, pantothenic, Vitamin D, and mixtures thereof may be used.

Cleaning Compositions

The skin cleaning compositions of the present invention comprise, in addition to the chelating agent, a cosmetically-acceptable surfactant. The term "cosmetically-acceptable surfactant" refers to a surfactant which is not only an effective skin cleanser, but also can be used without undue toxicity, irritation, allergic response, and the like. Furthermore, the surfactant must be capable of being commingled with the chelating agent in a manner such that there is no interaction which would substantially reduce the efficacy of the composition for protecting the skin from the effects of UV radiation.

The skin cleaning compositions of the present invention contain from about 1% to about 25%, preferably from about 5% to about 10%, of the chelating agent and from about 1% to about 90%, preferably from about 50% to about 85%, of a cosmetically-acceptable surfactant.

The physical form of the skin cleansing compositions is not critical. The compositions can be, for example, formulated as toilet bars, liquids, pastes, or mousses. Toilet bars are most preferred since this is the form of cleansing agent most commonly used to wash the skin.

The surfactant component of the compositions of the present invention are selected from anionic, nonionic, zwitterionic, amphoteric and ampholytic surfactants, as well as mixtures of these surfactants. Such surfactants are well-known to those skilled in the detergency art.

The cleaning compositions of the present invention can optionally contain, at their art-established levels, materials which are conventionally used in skin cleansing compositions.

Conventional antibacterial agents and sanitizers can be included in the skin cleansing compositions at levels of from about 0.5% to about 4%. Typical antibacterial sanitizers which are suitable for use herein include 3,4-di- and 3,4',5'-tri-bromosalicylanilides; 4,4'-dichloro- 3-(trifluoromethyl)carbanilide; 3,4, 4'-trichlorocarbanilide and mixtures of these materials. Use of these and related materials in skin cleansing compositions is described in more detail in Reller, et al., U.S. Pat. No. 3,256,200, issued Jun. 14, 1966, incorporated herein by reference.

Nonionic emollients can be included as skin conditioning agents in the skin cleansing compositions of the present invention at levels up to about 10%. Such materials include for example, mineral oils, paraffin wax having a melting point of from about 100° F. to about 170° F., fatty sorbitan esters (see U.S. Pat. No. 3,988,255, Seiden, issued Oct. 26, 1976, incorporated by reference herein), lanolin and lanolin derivatives, esters such as isopropyl myristate and triglycerides such as coconut oil or hydrogenated tallow.

Free fatty acid, such as coconut oil fatty acid, can be added to the compositions herein at levels up to about 10% to improve the volume and quality (creaminess) of the lather produced by the compositions.

Perfumes, dyes and pigments can also be incorporated into the skin cleansing compositions of the invention. Perfumes are preferably used at levels of from about 0.5% to 3%, and dyes and pigments are preferably used at levels of from about 0.001% to about 0.5%.

A particularly preferred optional ingredient is a cationic or nonionic polymeric skin feel aid. Reduced skin irritation benefits of both types of polymers are set out in "Polymer JR for Skin Care" Bulletin, by Union Carbide, 1977.

In addition to the aforementioned components, optional humectants, thickening agents, preservatives, alkaline agents, the skin conditioning propoxylated glycerol derivatives, or cosmetic adjuvants may also be used in the skin cleansing compositions.

The skin cleansing compositions of the present invention preferably also comprise a substantivity agent to prevent wash-off and to assure deposition of the chelating agent onto the skin. Suitable substantivity agents are guar gum and Polymer JR.

Combination Actives

Sunscreens

Optimum protection against sun damage can be obtained by using a combination of the non-sunscreening photoprotection agent of the present invention together with sunscreens. The photoprotecting capability of the chelating agent is primarily against UVB radiation. Thus, the combination of the chelating agent with a UVA sunscreen would be most desirable. Additional UVB protection may also be included in such compositions. The inclusion of sunscreens in compositions of the present invention at low levels will not significantly reduce the tanning response of the user but will enhance immediate protection against acute UV damage.

A wide variety of conventional sunscreening agents are suitable for use in combination with the chelating agent. Segatin, et al., at Chapter VIII, pages 189 et seq., of *Cosmetics Science and Technology,* disclose numerous suitable agents. Specific suitable sunscreening agents include, for example: p-Aminobenzoic acid, its salts and its derivatives (ethyl, isobutyl, glyceryl esters; p-dimethylaminobenzoic acid); Anthranilates (i.e., o-aminobenzoates; methyl, menthyl, phenyl, benzyl, phenylethyl, linalyl, terpinyl, and cyclohexenyl esters); Salicylates (amyl, phenyl, benzyl, menthyl, glyceryl, and dipropyleneglycol esters); Cinnamic acid derivatives (menthyl and benzyl esters, -phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naphtholsulfonates (sodium salts of 2-naphthol3,6-disulfonic and of 2-naphthol-6,8-disulfonic acids); Dihydroxy-naphthoic acid and its salts; o- and p-Hydroxybiphenyldisulfonates; Coumarin derivatives (7-hydroxy, 7-methyl, 3-phenyl); Diazoles ( 2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbityl) (6-propyl piperonyl) ether; Hydroquinone; Benzophenones (Oxybenzene, Sulisobenzone, Dioxybenzone, Benzoresorcinol, 2,2',4,4 '- Tetrahydroxybenzophenone, 2,2+-Dihydroxy-4,4'-dimethoxybenzophenone, Octabenzone; 4-Isopropyldibenzoylmethane; Butylmethoxydibenzoylmethane; Etocrylene; and 4-isopropyl-di-benzoylmethane.

Of these, 2-ethylhexyl p-methoxycinnamate, 4,4 '-t-butyl methoxydibenzoylmethane, 2-hydroxy-4-methoxybenzophenone, octyldimethyl p-aminobenzoic acid, digalloyltrioleate, 2,2-dihydroxy- 4-methoxybenzophenone, ethyl 4-[bis(hydroxypropyl)] aminobenzoate, 2-ethylhexyl2-cyano-3,3-diphenylacrylate, 2-ethylhexylsalicylate, glyceryl p-aminobenzoate, 3,3,5-trimethylcyclohexylsalicylate, methylanthranilate, p-dimethyl- aminobenzoic acid or aminobenzoate, 2-ethylhexyl p-dimethylamino- benzoate, 2-phenylbenzimidazole-5-sulfonic acid 2-(p-dimethylaminophenyl)-5-sulfonicbenzoxazoic acid and mixtures of these compounds, are particularly useful.

Preferred sunscreens useful in the compositions of the present invention are 2-ethylhexyl p-methoxycinnamate, butylmethoxydibenzoylmethane, 2-hydroxy-4-methoxybenzophenone, octyldimethyl p-aminobenzoic acid and mixtures thereof.

A safe and photoprotectively effective amount of sunscreen may be used in the chelating agent compositions of the present invention. By "safe and photoprotectively" is meant an amount sufficient to provide photoprotection when the composition is applied but not so much as to cause any side effects or skin reactions. The sunscreening agent must also be compatible with the chelating agent. By "compatible" is meant that the sunscreening agent must be capable of being commingled with the chelating agent in a manner such that there is no interaction which would substantially reduce the efficacy of the composition for photoprotection. Generally from about 1% to about 20%, preferably from about 2% to about 10%, of the composition may comprise a sunscreening agent. Exact amounts will vary depending upon the sunscreen chosen and the desired Sun Protection Factor (SPF).

SPF is a commonly used measure of photoprotection of a sunscreen against erythema. This number is derived from another parameter, the minimal erythemal dose (MED). MED is defined as the "least exposure dose at a specified wavelength that will elicit a delayed erythema response." The MED indicates the amount of energy reaching the skin and the responsiveness of the skin to the radiation. The SPF of a particular photoprotector is obtained by dividing the MED of protected skin by the MED of unprotected skin. The higher the SPF, the more effective the agent in preventing sunburn. The SPF value tells how many times longer a person can stay in the sun with use of the sunscreen (compared to a person with unprotected skin) before that person will experience 1 MED. For example, utilizing a sunscreen with an SPF of 6 will allow an individual to stay in the sun six times longer before receiving 1 MED. As the SPF value of a sunscreen increases, the less chance exists for development of tanning of the skin. Commercially available sunscreening products have SPF values ranging from 2 to 34.

A chelating agent's photoprotecting capability against erythema can also be measured. A chelating agent provides erythema reduction equivalent to an SPF-2 sunscreen. When an SPF-2 sunscreen agent is utilized with a chelating agent for protection against sunburn, the combination provides protection equivalent to an SPF-4 sunscreen.

Also particularly useful in the present invention are sunscreens such as those disclosed in Sabatelli, U.S. patent application Ser. No. 054,085 (filed Jun. 2, 1987) and Sabatelli et al., U.S. patent application Ser. No 054,046 (filed Jun. 2, 1987). The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

These sunscreening agents provide higher efficacy, broader UV absorption, lower skin penetration and longer lasting efficacy relative to conventional sunscreens.

Preferred members of this class of sunscreening agents are 4-N,N-(2-ethylhexyl)methylaminobenzoic acid ester of 2,4-dihydroxybenzophenone; N,N-di-(2-ethylhexyl)-4-aminobenzoic acid ester with 4-hydroxydibenzoylmethane; 4-N,N-( 2-ethylhexyl) methylaminobenzoic acid ester with 4-hydroxydibenzoylmethane; 4-N,N-(2-ethylhexyl)methylaminobenzoic acid ester of 2-hydroxy- 4-(2-hydroxyethoxy)benzophenone; 4-N,N-( 2-ethylhexyl) methylaminobenzoic acid ester of 4-(2-hydroxyethoxy)dibenzoylmethane; N-N-di-(2-ethylhexyl)-4-aminobenzoic acid ester of 2-hydroxy- 4-(2-hydroxyethoxy)benzophenone; and N,N-di-( 2-ethylhexyl)-4-aminobenzoic acid ester of 4-(2-hydroxyethoxy)dibenzoylmethane and mixtures thereof.

The compositions of the present invention, with or without sunscreens, may also be formulated as shampoos, conditioners, mousses or other hair care products. It is known that UV radiation damages hair and the photoprotecting agents of the present invention may minimize such damage. Furthermore such formulations will provide a means for applying the photoprotecting agents of the present invention onto the scalp, which is also susceptible to UV damage. Any compatible art-recognized hair care formulations can be used with the chelating agent added at a level of from about 1% to about 5%. If desired, a sunscreen may also be included at from about 1% to about 5%.

An agent may also be added to any of the compositions of the present invention to improve the skin substantivity of those compositions, particularly to enhance their resistance to being washed off by water, or rubbed off. A preferred agent which will provide this benefit is a copolymer of ethylene and acrylic acid. Compositions comprising this copolymer are disclosed in U.S. Pat. No. 4,663,157, Brock, issued May 5, 1987, which is incorporated herein by reference. The disclosed skin substantivity agent comprises the polymeric form of two monomers, ethylene and acrylic acid, to yield the following:

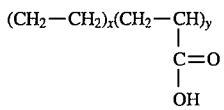

wherein the ratio of x:y is from about 1:24 to about 1:9, and wherein the weight average molecular weight of the molecule is from about 3500 to about 4500, preferably from about 4000 to about 4300. These copolymers are preferably included in an oil-in-water emulsion sunscreen composition comprising: a) from about 1% to about 20% of the chelating agent plus an optional oil-soluble sunscreen; b) from about 0.25% to about 3% of the ethylene-acrylic acid copolymer as described above; c) from about 2% to about 10% of an emulsifier; and d) from about 70% to about 90% of water, wherein the ratio of photoprotecting agents to the copolymer is from about 12:1 to about 15:1. Sunscreening agents which are particularly useful in combination with these copolymers are 2-ethylhexyl p-methoxycinnamate, butyl methoxydibenzoylmethane, 2-hydroxy-4-methoxybenzophenone, octyldimethyl p-aminobenzoic acid and mixtures thereof.

Anti-Inflammatory Agents

In a preferred photoprotection composition of the present invention, an anti-inflammatory agent is included as an active along with the chelating agent. The inclusion of an anti-inflammatory agent enhances the photoprotection benefits of the compositions. The anti-inflammatory agent protects strongly in the UVA radiation range (though it also provides some UVB protection as well), while the chelating agent protects strongly in the UVB radiation range. Thus the combination provides broad protection. The topical use of anti-inflammatory agents to reduce the effects of acute exposure, i.e., erythema, to UV radiation is known. However, it has now been discovered that the chronic use of anti-inflammatories also greatly reduces photo-aging of the skin resulting from chronic exposure to UV radiation. It has also been discovered that the combination of an anti-inflammatory agent and the chelating agent provides greater photoprotection than is provided by each active alone. Furthermore, the combination provides greater photoprotection than is provided by the sum of the effects of each active alone. By greater photoprotection is meant both reduction of acute effects of UV exposure, e.g., erythema, and reduction of chronic effects of UV exposure, e.g., premature wrinkling and sagging of the skin.

A safe and photoprotectively effective amount of an anti-inflammatory agent may be added to the compositions of the present invention. By "safe and photoprotectively effective" amount is meant an amount sufficient to provide photoprotection when the composition is properly applied, but not so much as to cause any side effects or adverse skin reactions; generally from about 0.1% to about 10%, preferably from about 0.5% to about 5%, of the composition. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use in the present invention is hydrocortisone.

A second class of anti-inflammatory agents which is useful in the compositions of the present invention includes the nonsteroidal anti-inflammatory agents. The variety of compounds encompassed by this group are well-known to those skilled in the art. For detailed disclosure of the chemical structure, synthesis, side effects, etc., of non-steroidal anti-inflammatory agents, reference may be had to standard texts, including *Anti-inflammatory and Anti-Rheumatic Drugs*, K. D. Rainsford, Vol. I–III, CRC Press, Boca Raton, (1985), and *Anti-inflammatory Agents, Chemistry and Pharmacology*, 1, R. A. Scherrer, et al., Academic Press, New York (1974), incorporated herein by reference.

Specific non-steroidal anti-inflammatory agents useful in the composition of the present invention include, but are not limited to:

1) the oxicams, such as piroxicam, isoxicam, tenoxicam, sudoxicam, and CP-14,304;
2) the salicylates, such as aspirin, disalcid, benorylate, trilisate, safapryn, solprin, diflunisal, and fendosal;
3) the acetic acid derivatives, such as diclofenac, fenclofenac, indomethacin, sul indac, tolmetin, isoxepac, furofenac, tiopinac, zidometacin, acematacin, fentiazac, zomepiract, clidanac, oxepinac, and felbinac;
4) the fenamates, such as mefenamic, meclofenamic, flufenamic, niflumic, and tolfenamic acids;
5) the propionic acid derivatives, such as ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, and tiaprofenic; and
6) the pyrazoles, such as phenybutazone, oxyphenbutazone, feprazone, azapropazone, and trimethazone.

Mixtures of these non-steroidal anti-inflammatory agents may also be employed, as well as the pharmaceutically-acceptable salts and esters of these agents. For example, etofenamate, a flufenamic acid derivative, is particularly useful for topical application. Of the nonsteroidal anti-inflammatory agents, ibuprofen, naproxen, flufenamic acid, mefenamic acid, meclofenamic acid, piroxicam and felbinac are preferred; ibuprofen, naproxen, and flufenamic acid are most preferred.

Another class of anti-inflammatory agents which are useful in the present invention are the anti-inflammatory agents disclosed in U.S. patent application Ser. No. 879,863, Loomans et al., filed Jun. 27, 1986. This application discloses a class of non-steroidal anti-inflammatory compounds which comprise specifically substituted phenyl compounds, especially substituted 2,6-di-tert-butyl phenol derivatives. For example, compounds selected from 4-(4'-pentyn-3'-one)- 2,6-di-t-butylphenol; 4-(5'-hexynoyl)- 2,6-di-t-butylphenol; 4-((S)-(–)-3'-methyl- 5'-hexynoyl)-2,6-di-t-butylphenol; 4-((R)-(+)- 3'-methyl-5'-hexynoyl)-2,6-di-t-butylphenol; and 4-(3',3'-dimethoxypropionyl)- 2,6-di-t-butylphenol are useful in the present invention.

Yet another class of anti-inflammatory agents which are useful in the present invention are those disclosed in U.S. patent application Ser. No. 051,446, Mueller, filed May 18, 1987. This application discloses compounds and diastereomeric mixtures of specific 2-naphthyl- containing ester compounds, especially naproxen ester and naproxol ester compounds, having two or more chiral centers. For example, compounds selected from (S)-naproxen-(S)-2-butyl ester, (S)-naproxen-(R)-2-butylester, (S)-naproxol-(R)- 2-methyl butyrate, (S)-naproxol-(S)-2-methyl butyrate, diasteromeric mixtures of (S)-naproxen-(S)-2-butyl ester and (S)-naproxen-(R)-2-butyl ester, and diasteromeric mixtures of (S)-naproxol-(R)-2-methyl butyrate and (S)-naproxol-(S)-2-methyl butyrate are useful in the present invention.

Finally, so-called "natural" anti-inflammatory agents are useful in the present invention. For example, candelilla wax, alpha bisabolol, aloe vera, Manjistha (extracted from plants in the genus *Rubia*, particularly *Rubia Cordifolia*), and Guggal (extracted from plants in the genus *Commiphora*, particularly *Commiphora Mukul*), may be used.

An even more preferred composition of the present invention comprises a chelating agent, a sunscreen, and an anti-inflammatory agent together for photoprotection. Such a composition comprises from about 1% to about 10%, preferably from about 2% to about 5%, of the chelating agent; from about 1% to about 15%, preferably from about 2% to about 10%, of a sunscreen; and from about 0.2% to about 5%, preferably from about 0.5% to about 2%, of an anti-inflammatory agent. This combination gives protection broader than that provided with each photoprotector alone. Furthermore, the combination provides greater photoprotection than is provided by the sum of the effects of each active alone. By greater photoprotection is meant both reduction of acute effects of UV exposure, e.g., erythema, and reduction of chronic effects of UV exposure, e.g., premature wrinkling and sagging of the skin. The photoprotection compositions of the present invention may comprise, in addition to the chelating agent, a safe and photoprotectively effective amount of a radical scavenging compound. By "safe and photoprotectively effective amount" is meant an amount sufficient to provide photoprotection when the composition is properly applied, but not so much as to cause any side effects or adverse skin reactions; generally from about 1% to about 20%, preferably from about 2% to about 10%, of the composition. Examples of such radical scavenging compounds are ascorbic acid (Vitamin C) and its salts, tocopherol (Vitamin E), other tocopherol esters, butylated hydroxy benzoic acids and their salts, 6-hydroxy-2,5,7,8-tetramethylchroman- 2-carboxylic acid (commercially available under the tradename Trolox®), gallic acid and its alkyl esters, especially propyl gallate, uric acid and its salts and alkyl esters, sorbic acid and its salts, the ascorbyl esters of fatty acids, amines (e.g., N,N-diethylhydroxylamine, aminoguanidine), sulfhydryl compounds (e.g., glutathione), and dihydroxyfumaric acid and its salts. Each of these compounds has photoprotecting capabilities. However, the use of the radical scavenger tocopherol sorbate in the present invention in combination with the chelating agent is preferred.

From about 1% to about 5% of these radical scavenging compounds may be used in the present invention in combination with the levels of chelating agent taught herein. Exact amounts will vary depending on which particular compound is used as these compounds vary somewhat in potency.

Method For Preventing Deleterious Effects Caused By UV Exposure

The present invention further relates to a method for protecting the skin of humans and lower animals from the deleterious effects of UV radiation. Such protection by the chelating agent extends not only to damage resulting from acute UV exposure, e.g. erythema, but also to damage resulting from chronic UV exposure, e.g. photoaging.

Such a method comprises applying to the skin of the human or lower animal a safe and photoprotectively effective amount of the specifically defined chelating agents which meet the criteria described supra. This may be accomplished by using a composition comprising of the chelating agent as described in the present application. The term "safe and photoprotectively effective amount", as used here (and hereinafter regarding other types of agents), means an amount of agent sufficient to substantially reduce the deleterious effects of UV-radiation to skin but not so much as to cause serious side effects or adverse skin reactions. Typically a safe and photoprotectively effective amount is from about 0.001 mg to about 1.0 mg, preferably from about 0.01 mg to about 0.5 mg, more preferably from about 0.05 mg to about 0.1 mg of the chelating agent per $cm^2$ skin. The chelating agent may be simply spread or sprayed onto the skin or may preferably be rubbed into the skin to enhance penetration. The chelating agent is applied in conjunction with UV exposure. The chelating agent works best if applied prior to or concomitantly with UV exposure. In addition, because of the mechanism by which the chelators appear to work (i.e., the chelation of metal ion formed in the skin), the chelating agents may also provide benefits if applied after UV exposure. Such application may take place several hours after UV exposure (e.g., nightly application of a skin moisturizing product), but preferably takes place within about 30 minutes after UV exposure. However, unlike typical sunscreens, which must remain as a coating on the skin throughout UV exposure, the application of the chelating agent may be done up to four hours prior to exposure. This is because the active agent penetrates the skin to work and thus is not as susceptible to rub-off, wash-off or wear-off. For protection against acute damage from UV-radiation, application of the chelating agent just prior to exposure is preferred. For protection against chronic damage from UV-radiation, application of the chelating agent several times daily; generally from about 2 times to about 5 times, preferably 2 times daily is preferred.

A preferred method of the present invention for preventing deleterious effects caused by UV exposure involves applying both a safe and photoprotectively effective amount of a chelating agent and a safe and photoprotectively effective amount of a sunscreening agent (as defined hereinbefore) to the skin simultaneously. By "simultaneous application" or "simultaneously" (as used here and hereinafter regarding other combinations of agents) is meant applying the agents to the skin at the same situs on the body at about the same time; though this can be accomplished by applying the agents separately to the skin, preferably a composition comprising all agents commingled is applied to the skin. The amount of sunscreening agent applied is generally from about 0.01 mg to about 1.0 mg, preferably from about 0.05 mg to about 0.5 mg, per $cm^2$ of skin.

The chelating agent and sunscreening agent may be simply spread over the skin, or rubbed into the skin to enhance penetration of the chelating agent. The actives are applied in conjunction with UV exposure, i.e., prior to, during, or after UV-exposure. For protection against acute damage from UV-radiation, application of the actives just prior to exposure is sufficient. For protection against chronic damage from UV radiation, application 2 to 5 times daily, preferably, about 2 times daily, is preferred.

Another method of the present invention for preventing deleterious effects caused by UV exposure involves applying both a safe and photoprotectively effective amount of a chelating agent and a safe and photoprotectively effective amount of tocopherol sorbate to the skin simultaneously. The amount of tocopherol sorbate applied is generally from about 0.01 mg to about 1.0 mg, preferably from about 0.05 mg to about 0.5 mg, per $cm^2$ skin.

The chelating agent and tocopherol sorbate may be simply spread over the skin or may preferably be rubbed into the skin to enhance penetration. The actives are applied in conjunction with UV exposure, i.e., prior to, during or after UV exposure. For protection against acute damage from UV-radiation, application of the actives just prior to exposure is sufficient. For protection against chronic damage from UV-radiation, application 2 to 5 times daily, preferably, about 2 times daily is preferred.

Yet another method of the present invention for preventing deleterious effects caused by UV exposure involves applying a safe and photoprotectively effective amount of a chelating agent, a safe and photoprotectively effective amount of tocopherol sorbate, and a safe and photoprotectively amount of a sunscreening agent to the skin simultaneously. The amount of each agent applied is generally from about 0.01 mg to about 1.0 mg, preferably from about 0.05 mg to about 0.5 mg, of the chelating agent; from about 0.01 mg to about of the 1.0 mg, preferably from about 0.05 mg to about 0.5 mg, tocopherol sorbate; and from about 0.01 mg to about 1.0 mg, preferably from about 0.05 mg to about 0.5 mg, sunscreening agent per $cm^2$ skin.

These agents may simply be spread over the skin or may preferably be rubbed into the skin to enhance penetration. The actives are applied in conjunction with UV exposure, i.e., prior to, during or after UV exposure. For protection against acute UV-radiation, application of the actives just prior to exposure is sufficient. For protection against chronic damage from UV-radiation, application several times daily, e.g., from about 2 times to about 5 times, preferably about 2 times daily, is recommended.

A preferred method of the present invention for preventing deleterious effects caused by UV exposure involves applying both a safe and photoprotectively effective amount of a chelating agent and safe and photoprotectively effective amount of an anti-inflammatory agent to the skin simultaneously. The amount of each agent is generally from about 0.005 mg to about 0.5 mg, preferably from about 0.01 mg to about 0.1 mg, anti-inflammatory agent per $cm^2$ skin; and from about 0.01 mg to about 1.0 mg, preferably from about 0.05 mg to about 0.5 mg, of the chelating agent per $cm^2$ skin. The chelating agent and anti-inflammatory agent may be simply spread over the skin or may preferably be rubbed into the skin to enhance penetration.

The combination of chelating agent plus anti-inflammatory agent may be applied prior to, concomitantly with, or after UV exposure. More specifically, the combination may be applied up to about 4 hours prior to UV exposure, up to about 30 minutes after UV exposure, or any time in between. This is because the anti-inflammatory agent works to minimize adverse reactions in the skin even if applied after UV exposure. For protection against acute damage from UV-radiation, application of the chelating agent and the anti-inflammatory agent just prior to exposure, or immediately following exposure, is sufficient. For protection against chronic damage from UV-radiation, application of the chelating agent and the anti-inflammatory agent several times daily, e.g., from about times to about 5 times, preferably about 2 times daily, is preferred.

Yet another method of the present invention for preventing deleterious effects caused by UV exposure involves applying a safe and photoprotectively effective amount of a chelating agent, a safe and photoprotectively effective amount of an anti-inflammatory agent, and a safe and photoprotectively effective amount of sunscreening agent to the skin simultaneously. The amount of each agent is generally from about 0.01 mg to about 1.0 mg, preferably from about 0.05 mg to about 0.5 mg of the chelating agent per $cm^2$ skin; from about 0.005 mg to about 0.5 mg, preferably from about 0.01 mg to about 0.1 mg, anti-inflammatory agent per $cm^2$ skin; and from about 0.01 mg to about 1.0 mg, preferably from about 0.05 mg to about 0.5 mg, sunscreening agent per $cm^2$ skin. The chelating agent, anti-inflammatory agent, and sunscreening agent may be simply spread over the skin or may preferably be rubbed into the skin to enhance penetration. The combination is applied in conjunction with UV exposure, i.e., prior to, concomitantly with, or after UV exposure. More specifically, the combination may be applied up to about 4 hours prior to UV exposure, up to about 30 minutes after UV exposure, or any time in between.

For protection against acute damage from UV-radiation, application of the chelating agent, the anti-inflammatory agent, and the sunscreening agent just prior to UV exposure is sufficient. For protection against chronic damage from UV-radiation, application of the chelating agent, the anti-inflammatory agent, and the sunscreening agent several times daily, e.g., from about 2 times to about 5 times, preferably about 2 times daily, is preferred.

Yet another method of the present invention for preventing deleterious effects caused by UV exposure involves applying a safe and photoprotectively effective amount of chelating agent, a safe and photoprotectively effective amount of tocopherol sorbate, a safe and photoprotectively effective amount of a sunscreening agent, and a safe and photoprotectively effective amount of an anti-inflammatory agent to the skin simultaneously. The amount of each agent is generally from about 0.01 mg to about 1 mg, preferably from about 0.05 mg to about 0.5 mg, of the chelating agent; from about 0.01 mg to about 1.0 mg, preferably from about 0.05 mg to about 0.5 mg, tocopherol sorbate; from about 0.01 mg to about 1.0 mg, preferably from about 0.05 mg to about 0.5 mg, sunscreening agent; and from about 0.005 mg to about 0.5 mg, preferably from about 0.01 mg to about 0.1 mg, anti-inflammatory agent per $cm^2$ skin.

These agents may simply be spread over the skin or may preferably be rubbed into the skin to enhance penetration. The actives may be applied prior to, concomitantly with, or after UV exposure. For protection against acute UV-radiation, application of the actives just prior to exposure, or immediately after exposure is sufficient. For protection against chronic damage from UV-radiation, application several times daily, e.g., from about 2 times to about 5 times, preferably about 2 times daily is recommended.

The following examples further describe and demonstrate the preferred embodiments within the scope of the present invention. The examples are given solely for the purpose of illustration, and are not to be construed as limitations of the present invention since many variations thereof are possible without departing from its spirit and scope.

All percentages and ratios herein are by weight, unless otherwise specified.

EXAMPLE 1

A moisturizing lotion is prepared by combining the following components utilizing conventional mixing techniques.

| Components | Percent by Weight of Composition |
|---|---|
| Water (purified) | 70.94 |
| Carbomer viscosity control agents (commercially available in the Acritamer series from R.I.T.A. Corp.) | 0.23 |
| Alkyl Parabens | 0.90 |
| Glycerin | 3.50 |
| Potassium Hydroxide | 0.09–0.15 |
| Tetrasodium EDTA | 0.10 |
| Cetyl Alcohol | 1.25 |
| Stearic Acid | 0.75 |
| Glyceryl Stearate | 0.63 |
| Polyoxyethylene Stearyl Alcohol (commercially available in the Brij series from ICI Americas, Inc.) | 1.75 |
| Coco-Caprylate/caprate | 2.00 |
| $C_{12}$-$C_{15}$ Alcohol Benzoate (Finsolv TN-commercially available from Finetex, Inc.) | 2.00 |
| Pyroctone Olamine | 2.00 |
| Octyl Methoxycinnamate | 7.50 |
| Benzophenone-3 | 1.00 |
| Octyl Dimethyl PABA | 1.00 |
| Dimethicone | 0.30 |
| Imidazolidinyl Urea | 0.10 |
| Ethylene Acrylate Copolymer | 3.80 |
| Tyrosine | 0.10 |

This lotion may be topically applied to inhibit damage caused by acute or chronic UV exposure. Use of an amount of lotion sufficient to deposit about 0.5 mg/cm$^2$ of pyroctone olamine, and about 0.5 mg/cm$^2$ of the sunscreening agents to the skin immediately prior to UV exposure is appropriate. Substantially similar results are obtained if the lotion is applied to the skin up to 4 hours prior to UV exposure or up to 30 minutes after UV exposure.

Substantially similar results are obtained if the pyroctone olamine is replaced, in whole or in part, with 2,2'-dipyridylamine; o-phenanthroline, di-2-pyridylketone; 2-furildioxime; 2,3-bis(2-pyridyl)pyrazine; 2,3-dihydroxybenzoic acid; ethylenediamine-N,N-bis-(2-hydroxyphenylacetic acid), dimethyl ester; 1,1'-carbonyldiimidazole; 1,2-dimethyl- 3-hydroxypyrid-4-one; 2,4,6-tri(2-pyridyl)-1,3,5-triazine; 1-pyrrolidinecarbodithioic acid; diethyldithiocarbamic acid; or Ciclopirox or mixtures thereof.

Substantially similar results are obtained if the octyl methoxycinnamate, benzophenone-3, and octyl dimethyl PABA are replaced, in whole or in part, with 2-ethylhexyl p-methoxycinnamate, butylmethoxydibenzoylmethane, 2-hydroxy- 4-methoxy-benzophenone, and mixtures thereof.

EXAMPLE II

A skin lotion is prepared by combining the following components utilizing conventional mixing techniques.

| Component | Percent by Weight Of Composition |
|---|---|
| 4-N,N-(2-Ethylhexyl)methylaminobenzoic Acid Ester of 4-(2-Hydroxyethoxy)-dibenzoylmethane | 10.00 |
| Water (purified) | 45.54 |
| Dimethyl Isosorbide | 8.00 |
| Dioctyl Maleate | 8.00 |
| $C_{12–15}$ Alcohol Benzoate (Finsolv TN-commercially available from Finetex, Inc.) | 8.00 |
| Glycerin | 3.50 |
| Ethylene Acrylate Copolymer | 3.80 |
| Pyroctone Olamine | 2.00 |
| Tocopherol Sorbate | 2.00 |
| Cetyl Alcohol | 1.75 |
| Polyoxyethylene Stearyl Alcohol (commerically available in the Brij series from ICI Americas, Inc.) | 1.75 |
| Stearic Acid | 1.25 |
| Glyceryl Stearate | 1.13 |
| Alkyl Parabens | 0.90 |
| Titanium Dioxide | 0.40 |
| Dimethicone | 0.30 |
| Carbomer viscosity control agents (commercially available in the Acritamer series from R.I.T.A. Corp.) | 0.23 |
| Imidazolidinyl Urea | 0.10 |
| Potassium Hydroxide | 0.15 |
| Tyrosine | 0.10 |
| Tetrasodium EDTA | 0.10 |

This lotion is useful for topical application to inhibit damage caused by acute or chronic UV exposure. Use of an amount of lotion sufficient to deposit about 0.5 mg/cm$^2$ of pyroctone olamine, about 0.5 mg/cm$^2$ tocopherol sorbate, and about 0.5 mg/cm$^2$ of the sunscreening agents to the skin immediately prior to UV exposure is appropriate. Substantially similar results are obtained if the lotion is applied to the skin up 4 hours prior to UV exposure or up to 30 minutes after UV exposure.

Substantially similar results are obtained if the pyroctone olamine is replaced, in whole or in part, with 2,2'-dipyridylamine; o-phenanthroline, di-2-pyridylketone; 2-furildioxime; 2,3-bis(2-pyridyl)pyrazine; 2,3-dihydroxybenzoic acid; ethylenediamine-N,N-bis-(2-hydroxyphenylacetic acid), dimethyl ester; 1,1'-carbonyldiimidazole; 1,2-dimethyl- 3-hydroxypyrid-4-one; 2,4,6-tri(2-pyridyl)-1,3,5-triazine; 1-pyrrolidinecarbodithioic acid; diethyldithiocarbamic acid; or Ciclopirox, or mixtures thereof.

Substantially similar results are obtained if the tocopherol sorbate is replaced, in whole or in part, with ascorbic acid and its salts, tocopherol, tocopherol esters, butylated hydroxybenzoic acid and its salts, 6-hydroxy- 2,5,7,8-tetramethyl-chroman-2-carboxylic acid, gallic acid and its alkyl esters, uric acid and its salts and esters, sorbic acid and its salts, amines, sulfhydryl compounds, dihydroxyfumaric acid and its salts, or mixtures thereof.

Substantially similar results are obtained if the 4-N,N-( 2-ethylhexyl)methylaminobenzoic acid ester of 4-( 2-hydroxyethoxy)dibenzoylmethane is replaced, in whole or in part, with the 4-N,N-(2-ethylhexyl)methylaminobenzoic acid ester of 2,4-dihydroxybenzophenone, the N,N-di-(2-ethylhexyl)-4-aminobenzoic acid ester of 4-hydroxydibenzoylmethane, the 4-N,N-( 2-ethylhexyl)methylaminobenzoic acid 4-ester of 2-hydroxy-4-( 2-hydroxyethoxy)benzophenone, the 4-N,N-(2-ethylhexyl)methylaminobenzoic acid ester of 4-(2-hydroxyethoxy)dibenzoylmethane, the N-N-di-(2-ethylhexyl)-4-aminobenzoic acid ester of 2-hydroxy-4-(2- hydroxyethoxy)benzophenone, or the N,N-di-(2-ethylhexyl)-4-aminobenzoic acid ester of 4-(2-hydroxyethoxy)dibenzoylmethane, and mixtures thereof.

EXAMPLE III

A suntan cream is prepared by combining the following components utilizing conventional mixing techniques.

| Component | Percent by Weight of Composition |
| --- | --- |
| Mineral Oil | 20.00 |
| Octyl Palmitate | 10.00 |
| Glyceryl Isostearate | 4.00 |
| Octyl Methoxycinnamate | 7.50 |
| Oxybenzone | 3.00 |
| Polyethylene (AC-617-A,AC-6-A available from Allied Chemical) | 2.00 |
| Alkyl parabens | 0.30 |
| Glycerin | 2.00 |
| Pyroctone Olamine | 2.00 |
| Ibuprofen | 1.00 |
| Water (purified) | q.s. |

This cream is useful for topical application to inhibit damage caused by acute or chronic UV exposure. Use of an amount of cream sufficient to deposit about 0.5 mg/cm$^2$ of pyroctone olamine, about 0.5 mg/cm$^2$ of the sunscreening agents, and about 0.1 mg/cm$^2$ of ibuprofen to the skin immediately following UV-exposure is appropriate. Substantially similar results are obtained if the cream is applied to the skin up to 4 hours prior to UV exposure or up to 30 minutes following UV exposure.

Substantially similar results are obtained if the pyroctone olamine is replaced, in whole or in part, with 2,2'-dipyridylamine; o-phenanthroline, di-2-pyridyl ketone; 2-furildioxime; 2,3-bis(2-pyridyl)pyrazine; 2,3-dihydroxybenzoic acid; ethylenediamine-N,N-bis-(2-hydroxyphenylacetic acid), dimethyl ester; 1,1'-carbonyldiimidazole; 1,2-dimethyl- 3-hydroxypyrid-4-one; 2,4,6-tri(2-pyridyl)-1,3,5-triazine; 1-pyrrolidinecarbodithioic acid; diethyldithiocarbamic acid; or Ciclopirox or mixtures thereof.

Substantially similar results are obtained if the octyl methoxy-cinnamate and the oxybenzone are replaced, in whole or in part, with 2-ethylhexyl p-methoxycinnamate, butylmethoxydi benzoylmethane, 2-hydroxy-4-methoxy-benzophenone, and mixtures thereof.

Substantially similar results are obtained if the ibuprofen is replaced, in whole or in part, with hydrocortisone acetate, naproxen, flufenamic acid, mefenamic acid, meclofenamic acid, piroxicam, felbinac, 4-(4'-pentyn-3'-one)- 2,6-di-t-butylphenol, 4-(5'-hexynoyl)-2,6-di-t-butylphenol, 4-(S)-(–)-3'-methyl-5'-hexynoyl- 2,6-di-t-butylphenol, 4-(R)-(+)-3'-methyl- 5'-hexnoyl- 2,6-di-t-butylphenol, 4-(3',3'-dimethoxypropionyl)-2,6-di-t-butylphenol, Manjistha, Guggal, and mixtures thereof.

EXAMPLE IV

A suntan stick is prepared by combining the following components utilizing conventional mixing techniques.

| Component | Percent by Weight of Composition |
| --- | --- |
| Candelilla Wax | 19.25 |
| Ozokerite Wax | 19.25 |
| Petrolatum | 19.25 |
| Lanolin | 15.00 |
| Mineral Oil | 14.85 |
| Octyl Dimethyl PABA | 7.00 |
| Benzophenone-3 | 3.00 |
| BHA (preservative: butylated hydroxy anisole) | 0.05 |
| Propylparaben | 0.10 |
| Pyroctone Olamine | 5.00 |
| Flavor | q.s. |

This stick is useful for topical application, for example to the lips, to inhibit damage caused by acute or chronic UV exposure. Use of an amount of stick sufficient to deposit about 1.0 mg/cm$^2$ of pyroctone olamine, and about 0.5 mg/cm$^2$ of the sunscreening agents to the lips immediately prior to UV exposure is appropriate. Substantially similar results are obtained if the stick is applied up to 4 hours prior to UV exposure or up to 30 minutes after UV exposure.

Substantially similar results are obtained if the pyroctone olamine is replaced, in whole or in part, with 2,2'-dipyridylamine; o-phenanthroline, di-2-pyridylketone; 2-furildioxime; 2,3-bis(2-pyridyl)pyrazine; 2,3-dihydroxybenzoic acid; ethylenediamine-N,N-bis-(2-hydroxyphenylacetic acid), dimethyl ester; 1,1'-carbonyldiimidazole; 1,2-dimethyl- 3-hydroxypyrid-4-one; 2,4,6-tri(2-pyridyl)-1,3,5-triazine; 1-pyrrolidinecarbodithioic acid; diethyldithiocarbamic acid; or Ciclopirox, or mixtures thereof.

Substantially similar results are obtained if the octyl dimethyl PABA and the benzophenone-3 are replaced, in whole or in part, with 2-ethylhexyl p-methoxycinnamate, butylmethoxy-di-benzoylmethane, 2-hydroxy-4-methoxy-benzophenone, and mixtures thereof.

EXAMPLE V

A low SPF suntan cream is prepared by combining the following components utilizing conventional mixing techniques.

| Component | Percent by Weight of Composition |
| --- | --- |
| Tetrasodium EDTA | 0.05 |
| Alkylparabens | 0.30 |
| Carbopol (polyacrylic acid polymer-commercially available from B. F. Goodrich Chemical) | 0.20 |
| Glycerin | 2.00 |
| Laureth-23 (polyethylene glycol ether of lauryl alcohol) | 3.00 |
| Sorbitan Stearate | 1.50 |
| Octyl Dimethyl PABA | 3.00 |
| Dimethicone | 2.00 |
| Stearyl Alcohol | 6.00 |
| Triethanolamine | 0.20 |
| Pyroctone Olamine | 2.00 |
| Water (purified) | q.s. |

This cream is useful for topical application to inhibit damage caused by acute or chronic UV exposure. Use of an amount of cream sufficient to deposit about 0.5 mg/cm$^2$ of pyroctone olamine, and about 0.5 mg/cm$^2$ of the sunscreening agents to the skin immediately prior to UV exposure is appropriate. Substantially similar results are obtained if the cream is applied to the skin up to 4 hours prior to UV exposure or up to 30 minutes after UV exposure.

Substantially similar results are obtained if the pyroctone olamine is replaced, in whole or in part, with 2,2'-dipyridylamine; o-phenanthroline, di-2-pyridylketone; 2-furildioxime; 2,3-bis(2-pyridyl)pyrazine; 2,3-dihydroxybenzoic acid; ethylenediamine-N,N-bis-(2-hydroxyphenylacetic acid), dimethyl ester; 1,1'-carbonyldiimidazole; 1,2-dimethyl- 3-hydroxypyrid-4-one; 2,4,6-tri(2-pyridyl)-1,3,5-triazine; 1-pyrrolidinecarbodithioic acid; diethyldithiocarbamic acid; or Ciclopirox, or mixtures thereof.

Substantially similar results are obtained if the octyl dimethyl PABA is replaced, in whole or in part, with 2-ethylhexyl p-methoxycinnamate, butylmethoxydibenzoylmethane, 2-hydroxy- 4-methoxybenzophenone, and mixtures thereof.

EXAMPLE VI

A suntan aqueous face gel is prepared by combining the following components utilizing conventional mixing techniques.

| Component | Percent by Weight Of Composition |
|---|---|
| Water (purified) | 50.00 |
| Aloe | 38.00 |
| Carbopol | 1.00 |
| Glycerin | 3.00 |
| Methylparaben | 0.20 |
| Triethanolamine | 0.90 |
| 2-Phenyl-Benzimedoic Sulfonic Acid | 2.00 |
| Octoxynol-13 (ethoxylated alkyl phenol $(C_8H_{17})(C_6H_4)(OCH_2CH_2)_nOH$, n = av. val. 13) | 1.50 |
| Pyroctone Olamine | 2.00 |
| Color and Fragrance | q.s. |

This aqueous gel is useful for application to the face to inhibit damage caused by acute or chronic UV exposure. Use of an amount of gel to deposit about 0.5 mg/cm$^2$ of pyroctone olamine to the face immediately prior to UV exposure is appropriate. Substantially similar results are obtained if the gel is applied to the face up to 4 hours prior to UV exposure or up to 30 minutes after UV exposure.

Substantially similar results are obtained if the pyroctone olamine is replaced, in whole or in part, with 2,2'-dipyridylamine; o-phenanthroline, di-2-pyridylketone; 2-furildioxime; 2,3-bis(2-pyridyl)pyrazine; 2,3-dihydroxybenzoic acid; ethylenediamine-N,N-bis-(2-hydroxyphenylacetic acid), dimethyl ester; 1,1'-carbonyldiimidazole; 1,2-dimethyl- 3-hydroxypyrid-4-one; 2,4,6-tri(2-pyridyl)-1,3,5-triazine; 1-pyrrolidinecarbodithioic acid; diethyldithiocarbamic acid; or Ciclopirox, or mixtures thereof.

EXAMPLE VII

A suntan gel is prepared by combining the following components utilizing conventional mixing techniques.

| Component | Percent by Weight of Composition |
|---|---|
| Ozokerite Wax | 10.00 |
| Paraffin | 10.00 |
| Petrolatum | 10.00 |
| Isopropyl Myristate | 5.00 |
| Mineral Oil | 58.00 |
| Octyl Dimethyl PABA | 2.50 |
| Propylparaben | 0.10 |
| BHA | 0.05 |
| Pyroctone Olamine | 2.00 |
| Naproxen | 2.00 |
| Fragrance and Color | q.s. |

This suntan gel is useful for topical application to inhibit damage caused by acute or chronic UV exposure. Use of an amount of gel to deposit about 0.5 mg/cm$^2$ of pyroctone olamine, about 0.5 mg/cm$^2$ of the sunscreening agent, and about 0.1 mg/cm$^2$ of naproxen to the skin immediately following UV exposure is appropriate. Substantially similar results are obtained if the gel is applied to the skin up to 30 minutes after UV exposure or up to 4 hours prior to UV exposure or up to 30 minutes after UV exposure.

Substantially similar results are obtained if the pyroctone olamine is replaced, in whole or in part, with 2,2'-dipyridylamine; o-phenanthroline, di-2-pyridylketone; 2-furildioxime; 2,3-bis(2-pyridyl)pyrazine; 2,3-dihydroxybenzoic acid; ethylenediamine-N,N-bis-(2-hydroxyphenylacetic acid), dimethyl ester; 1,1'-carbonyldiimidazole; 1,2-dimethyl- 3-hydroxypyrid-4-one; 2,4,6-tri(2-pyridyl)-1,3,5-triazine; 1-pyrrolidinecarbodithioic acid; diethyldithiocarbamic acid; or Ciclopirox, or mixtures thereof.

Substantially similar results are obtained if the octyldimethyl PABA is replaced, in whole or in part, with 2-ethylhexyl p-methoxycinnamate, butylmethoxydibenzoylmethane, 2-hydroxy- 4-methoxybenzophenone, and mixtures thereof.

Substantially similar results are obtained if the naproxen is replaced, in whole or in part, with hydrocortisone acetate, ibuprofen, flufenamic acid, mefenamic acid, meclofenamic acid, piroxicam, felbinac, 4-(4'-pentyn-3'-one)- 2,6-di-t-butylphenol, 4-(5'-hexynoyl)-2,6-di-t-butylphenol, 4-(S)-(–)- 3'-methyl-5'-hexynoyl- 2,6-di-t-butylphenol, 4-(R)-(+)-3'-methyl- 5'-hexynoyl-2,6-di-t-butylphenol, 4-(3', 3'-dimethoxypropionyl)-2,6-di-t-butylphenol, Manjistha, Guggal, and mixtures thereof.

EXAMPLE VIII

A suntan oil is prepared by combining the following components utilizing conventional mixing techniques.

| Component | Percent by Weight of Composition |
|---|---|
| Sesame Oil | 5.0 |
| Cyclomethicone | 20.0 |
| Isopropyl Myristate | 5.0 |
| BHA | 0.05 |
| Sorbitan Oleate | 1.0 |
| Octyl Dimethyl PABA | 1.5 |
| Propylparaben | 0.7 |
| Pyroctone Olamine | 2.00 |
| Mineral Oil | q.s. |

This suntan oil is useful for topical application to inhibit damage caused by acute or chronic UV exposure. Use of an amount of oil sufficient to deposit about 0.5 mg/cm$^2$ of pyroctone olamine, and about 0.5 mg/cm$^2$ of the sunscreening agent to the skin immediately prior to UV exposure is appropriate. Substantially similar results are obtained if the oil is applied to the skin up to 4 hours prior to UV exposure or up to 30 minutes after UV exposure.

Substantially similar results are obtained if the pyroctone olamine is replaced, in whole or in part, with 2,2'-dipyridylamine; o-phenanthroline, di-2-pyridylketone; 2-furildioxime; 2,3-bis(2-pyridyl)pyrazine; 2,3-dihydroxybenzoic acid; ethylenediamine-N,N-bis-(2-hydroxyphenylacetic acid), dimethyl ester; 1,1'-carbonyldiimidazole; 1,2-dimethyl- 3-hydroxypyrid-4-one; 2,4,6-tri(2-pyridyl)-1,3,5-triazine; 1-pyrrolidinecarbodithioic acid; diethyldithiocarbamic acid; or Ciclopirox, or mixtures thereof.

Substantially similar results are obtained if the octyl dimethyl PABA is replaced, in whole or in part, with 2-ethylhexyl p-methoxycinnamate, butylmethoxydibenzoylmethane, 2-hydroxy- 4-methoxybenzophenone, and mixtures thereof.

EXAMPLE IX

A moisturizing oil-in-water-in-silicone sunscreen emulsion lotion is formed from the following ingredients.

| Ingredient | Percent by Weight of Composition |
| --- | --- |
| Aqueous Phase: | |
| Purified Water | 57.17 |
| Pantethine, 80% aq. soln. (humectant) | 0.10 |
| Methylparaben | 0.20 |
| Carbomer viscosity control agent (commercially available in the Acritamer series from R.I.T.A. Corp.) | 0.10 |
| Glycerin | 2.50 |
| Sodium alkyl polyether sulfonate (anionic emulsifier) | 0.10 |
| Oil Phase: | |
| Heavy mineral oil | 1.75 |
| Cholesterol | 1.00 |
| Cetyl palmitate | 0.20 |
| PEG-22/Dodecyl glycol copolymer | 0.20 |
| Ethylparaben | 0.10 |
| Propylparaben | 0.15 |
| Neutralizer Base: | |
| Triethanolamine | 0.10 |
| Color & Fragrance: | |
| FD&C Red No. 4 (1% aq. soln.) | 0.03 |
| Odorant Oil | 0.30 |
| Silicone Phase: | |
| Cyclomethicone/Dimethicone copolyol (90:10) | 9.50 |
| Cyclomethicone/Dimethiconol (13:87) | 5.00 |
| Cyclomethicone | 3.00 |
| Phenyl Dimethicone | 1.00 |
| Pareth-15-3 (polyethylene glycol ester of a mixed synthetic $C_{11}$–$C_{15}$ fatty alcohol, av. 3 moles EO) | 2.00 |
| Octyl Methoxycinnamate | 7.00 |
| Benzophenone-3 | 0.50 |
| Naproxen | 2.00 |
| Pyroctone Olamine | 2.00 |
| $C_{12-15}$ Alcohols Benzoate | 2.85 |

In a suitably sized vessel equipped with a suitable mechanical stirrer (Tekmar Model RW-20 stirring motor, manufactured by IKA-WERK, Germany), the water, pantethine, methylparaben, glycerine and sulfonate emulsifier are heated to about 72°–75° C. and mixed. Stirring is increased until a vortex forms in the aqueous solution. The thickener, Carbomer, is slowly added to the vortex and allowed to mix until completely hydrated and the resultant gel solution is free of gelatinous particles and is uniform in composition. The temperature is maintained at about 72°–75° C. with constant agitation.

The oil phase ingredients are added to a separate suitably sized vessel and heated to about 80°–85° C. using slow mechanical stirring once the oil phase becomes molten. At this point the sunscreening agents, naproxen, and pyroctone olamine are mixed in. When molten, agitation is maintained to keep the oil phase uniform during heating.

The heated oil phase is then slowly added to the heated water phase with stirring to form the oil-in-water emulsion. After addition is complete, the mechanical stirring means is slowed to avoid unnecessary aeration of the emulsion and mixing is continued for approximately fifteen minutes at 70°–75° C. The emulsion is then cooled to about 60° C. with moderate agitation. The base, triethanolamine, is then slowly added to neutralize the acidic Carbomer 940 and the emulsion (pH 6.5) is mixed at moderate speed until uniform. The homogeneous oil-in-water emulsion is then cooled to about 45°–50° C. and the colorant and odorant oil are added followed by cooling to room temperature (about 25° C.) with continued moderate agitation.

The four silicone fluids and other silicone phase ingredients are mixed together in a separate vessel until a uniform silicone phase is attained. The oil-in-water emulsion is slowly added to the silicone phase with stirring until a homogeneous oil-in-water-in-silicone double emulsion in lotion form is attained.

This moisturizing lotion is useful for topical application to inhibit damage caused by acute or chronic UV exposure. Use of an amount of lotion sufficient to deposit about 0.5 mg/cm$^2$ of pyroctone olamine, about 0.5 mg/cm$^2$ of sunscreening agents, and about 0.1 mg/cm$^2$ of naproxen to the skin immediately following UV exposure is appropriate. Substantially similar results are obtained if the lotion is applied to the skin up to 30 minutes after UV exposure or up to 4 hours prior to UV exposure. This lotion may also be applied several times daily, e.g., 2 or 3 times daily, for extended periods of time, i.e., greater than one week, in amounts sufficient to deposit about 0.5 mg/cm$^2$ of pyroctone olamine, about 0.5 mg/cm$^2$ of sunscreening agents, and about 0.1 mg/cm$^2$ of naproxen to the skin to inhibit damage caused by chronic UV exposure.

Substantially similar results are obtained if the pyroctone olamine is replaced, in whole or in part, 2,2'-dipyridylamine; o-phenanthroline, di-2-pyridylketone; 2-furildioxime; 2,3-bis(2pyridyl)pyrazine; 2,3-dihydroxybenzoic acid; ethylenediamine-N,N-bis-( 2-hydroxyphenylacetic acid), dimethyl ester; 1,1'-carbonyldiimidazole 1,2-dimethyl-3-hydroxypyrid-4-one; 2,4,6-tri(2-pyridyl)-1,3,5-triazine; 1-pyrrolidinecarbodithioic acid; diethyldithiocarbamic acid; or Ciclopirox, or mixtures thereof.

Substantially similar results are obtained if the octyl methoxycinnamate and benzophenone-3, are replaced, in whole or in part, with 2-ethylhexyl p-methoxycinnamate, butylmethoxy-dibenzoylmethane, 2-hydroxy-4-methoxybenzophenone, and mixtures thereof.

Substantially similar results are obtained if the naproxen is replaced, in whole or in part, with hydrocortisone acetate, ibuprofen, flufenamic acid, mefenamic acid, meclofenamic acid, piroxicam, felbinac, 4-(4'-pentyn-3'-one)- 2,6-di-t-butylphenol, 4-(5'-hexynoyl)-2,6-di-t-butylphenol, 4-(S)-(–)-3'-methyl-5'hexynoyl- 2,6-di-t-butylphenol, 4-(R)-(+)-3'-methyl- 5'hexynoyl-2,6-di-t-butylphenol, 4-(3',3'-dimethoxypropionyl)2,6-di-t-butylphenol, Manjistha, Guggal, and mixtures thereof.

EXAMPLE X

A skin conditioning toilet bar is prepared from the following ingredients.

| Component | Percent by Weight of Composition |
| --- | --- |
| Tallow/Coconut Soap (50/50) | 61.61 |
| Water | 10.00 |
| 2-Hydroxypropylglyceryl Ether | 4.00 |
| Sodium Coconut Glyceryl Ether Sulfonate | 8.80 |
| Coconut Fatty Acid (CnFA) | 4.00 |
| Pyroctone Olamine | 5.00 |
| Perfume | 1.40 |
| NaCl | 1.04 |
| $Na_2SO_4$ | 0.34 |
| $Na_4EDTA$ | 0.06 |
| $TiO_2$ | 0.20 |
| Jaguar C15 (quar hydroxy propyltrimonium chloride) | 1.00 |
| Merquat 550 (poly quaternium-7) | 1.00 |
| Minors (Colorants, Preservatives, Fillers, etc.) | 1.55 |

The above composition is prepared in the following manner.

Crutching Step

About 127.6 parts of a mix containing: 29.8% water, 52.7% 50/50 tallow/coconut (T/Cn) soap, 16.7% sodium coconut glyceryl ether sulfonate paste, 3.3% coconut free fatty acid (CnFA), 3.1% 2-hydroxypropylglyceryl ether, and 0.2% NaCl are heated to ca. 150°–200° F. (65°–94° C.). About 10.0 parts of the hydrated polymer JAGUAR C-15 are mixed in. The pyroctone olamine is then added and mixed in.

Vacuum Drying Step

The crutcher mix is vacuum dried at ca. 50 mm Hg absolute pressure to reduce the moisture content of the mix to ca. 10% and to plod this soap into noodles. These noodles are passed through a milling step once.

Amalgamating Step

The once-milled soap noodles are weighed and placed in a batch amalgamator. To about 99.1 parts noodles in the amalgamator are added: 0.20 part $TiO_2$, 1.4 parts perfume, 0.15 part colorant solution, 0.15 part of a solution which contains ca. 40% EDTA. The combined ingredients are mixed thoroughly.

Milling Step

Three-roll soap mills are set up with all rolls at 85°– 105° F. (29°–41° C.). The mixture from the amalgamator is passed through the mills several times to obtain a homogeneous mix. This is an intimate mixing step.

Plodding and Stamping Steps

A conventional plodder is set up with the barrel temperature at about 90° F. (32° C.) and the nose temperature at about 110° F. (43° C.). The plodder used is a dual stage twin screw plodder that allows for a vacuum of about 40 to 65 mm Hg between the two stages. The soap log extruded from the plodder is typically round or oblong in cross-section, and is cut into individual plugs. These plugs are then stamped on a conventional soap stamping apparatus to yield the finished toilet soap bar. The use of this toilet bar for cleansing provides a useful means for deposition of pyroctone olamine to the skin to inhibit damage caused by acute or chronic UV exposure. Use of the toilet bar such that about 0.05 mg/cm² of pyroctone olamine is deposited on the skin immediately prior to UV exposure is appropriate. Substantially similar results are obtained if the toilet bar is used up to 4 hours prior to UV exposure or up to 30 minutes after UV exposure.

Substantially similar results are obtained if the pyroctone olamine is replaced, in whole or in part, with 2,2′-dipyridylamine; o-phenanthroline, di-2-pyridylketone; 2-furildioxime; 2,3-bis(2-pyridyl)pyrazine; 2,3-dihydroxybenzoic acid; ethylenediamine-N,N-bis-(2-hydroxyphenylacetic acid), dimethyl ester; 1,1′-carbonyldiimidazole; 1,2-dimethyl- 3-hydroxypyrid-4-one; 2,4,6-tri(2-pyridyl)-1,3,5-triazine; 1-pyrrolidinecarbodithioic acid; diethyldithiocarbamic acid; or Ciclopirox, or mixtures thereof.

EXAMPLE XI

Facial Cleanser

A facial cleanser (lathering mousse composition) is prepared from the following ingredients.

| Emulsion Concentrate (A) | Percent by Weight of Composition |
| --- | --- |
| DRO Water[1] | 52.63 |
| 2-Hydroxypropyglyceryl Ether | 15.00 |
| Sodium Glyceryl Ether Sulfonate (90% Coconut/10 Tallow)-50% Active | 12.06 |
| Sodium Lauroyl Sarcosinate-33% Active | 6.66 |
| PEG 600 | 4.00 |
| Aloe Vera Gel | 1.00 |
| Lexein LP170P (hydrolyzed animal protein) | 1.00 |
| Stearic Acid | 1.00 |
| Citric Acid | 0.30 |
| Pyroctone Olamine | 5.00 |
| Jaguar C14-S (guar hydroxypropyltrimonium chloride) | 0.25 |
| Perfume | 0.20 |
| FD&C Red Dye #4 | 0.20 |
| Lauryl Alcohol | 0.20 |
| Alkyl Parabens | 0.30 |
| Germall 115 (Imidazolidinyl urea) | 0.10 |
| $Na_4EDTA$ | 0.10 |

[1]Water purified by double reverse osmosis

A-46 Propellant (Isobutane-Propane) (B)

(6.4 g in 100 g concentrate)

The composition is prepared in a single batch process. DRO water is brought to 71.1° C. and the Jaguar polymer is added with agitation. Maintaining agitation, the following ingredients are added sequentially: Sodium glycerol ether sulfonate, Sodium lauroyl sarcosinate, lauryl alcohol, PEG-600, Parabens, EDTA, dye, 2-Hydroxypropylglyceryl ether, stearic acid, Aloe Vera Gel, citric acid and pyroctone olamine. The mixture is then cooled to 135°– 140° F. and the following ingredients are added sequentially with stirring: Lexein, Germall and perfume. The resulting mixture is cooled to room temperature.

Aluminum cans are then filled with the cooled emulsion concentrate. Aerosol activator assemblies are then crimped onto the cans to form a tight seal. Pressurized A-46 Propellant is then pumped into the cans in an amount sufficient to provide a composition consisting of 6% propellant and 94% emulsion concentrate in each can.

Upon activation of the aerosol assembly, the composition is dispensed under pressure in the form of a creamy, foaming mousse which can be applied to the skin for cleansing and as a means for deposition of pyroctone olamine to the skin to inhibit damage caused by acute or chronic UV exposure. Use of amount of facial cleanser sufficient to deposit about 0.05 mg/cm² of pyroctone olamine to the skin immediately prior to UV exposure is appropriate. Substantially similar results are obtained if the cleanser is used up to 4 hours prior to UV exposure or up to 30 minutes after UV exposure.

EXAMPLE XII

A cream soap is prepared by combining the following ingredients as described below.

| Component | Percent by Weight of Composition |
| --- | --- |
| Sodium Lauroyl Glutamate (Acylglutamate LS-11) (28) | 22.00 |
| Sodium Hydrogenated Tallow Glutamate and Cocoyl Glutamate (Acylglutamate GS-11) (28) | 3.00 |
| Polyethylene Glycol 400 | 10.00 |
| Polyethylene Glycol (M.W. 6300) Monostearate | 5.00 |
| Polyoxyethylene (20) Sorbitan Monostearate | 3.00 |
| Pyroctone Olamine | 3.00 |
| Tocopherol Sorbate | 5.00 |
| Flufenamic Acid | 5.00 |
| 2-Ethylhexyl Methoxycinnamate | 3.00 |
| Water | 30.50 |
| Glycerin | 10.00 |
| Fragrance and Preservative | q.s. |

The sodium glutamate, sodium hydrogenated tallow glutamate and cocoyl glutamate, polyethylene glycol, polyethylene glycol monostearate, polyoxyethylene sorbitan monostearate, pyroctone olamine, tocopherol sorbate, flufenamic acid, 2-ethylhexyl methoxycinnamate, and water are dissolved together with heating. The glycerin is added with agitation. The mixture is cooled to about 60° C. and the fragrance and preservative are added. The mixture is cooled to 35° C. with agitation.

The result is a cream soap the use of which for cleansing provides a useful means for deposition of pyroctone olamine, tocopherol sorbate, flufenamic acid, and 2-ethylhexyl methoxycinnamate to the skin to inhibit damage caused by acute or chronic UV exposure. Use of an amount of cream soap sufficient to deposit about 0.05 mg/cm$^2$ of pyroctone olamine, 0.05 mg/cm$^2$ of tocopherol sorbate, 0.05 mg/cm$^2$ of the sunscreening agent, and 0.01 mg/cm$^2$ of flufenamic acid to the skin immediately following UV exposure is appropriate. Substantially similar results are obtained if the soap is used up to 30 minutes after UV exposure or up .to 4 hours prior to UV exposure.

Substantially similar results are obtained if the pyroctone olamine is replaced, in whole or in part, with 2,2 '-dipyridylamine; o-phenanthroline, di-2-pyridylketone; 2-furildioxime; 2,3-bis(2-pyridyl)pyrazine; 2,3-dihydroxybenzoic acid; ethylenediamine-N,N-bis-(2-hydroxyphenylacetic acid), dimethyl ester; 1,1'-carbonyldiimidazole; 1,2-dimethyl- 3-hydroxypyrid-4-one; 2,4,6-tri(2-pyridyl)-1,3,5-triazine; 1-pyrrolidinecarbodithioic acid; diethyldithiocarbamic acid; or Ciclopirox, or mixtures thereof.

Substantially similar results are obtained if the tocopherol sorbate is replaced, in whole or in part, with ascorbic acid and its salts, tocopherol, tocopherol esters, butylated hydroxybenzoic acid and its salts, 6-hydroxy-2,5,7,8-tetramethylchroman- 2carboxylic acid, gallic acid and its alkyl esters, uric acid and its salts and esters, sorbic acid and its salts, amines, sulfhydryl compounds, dihydroxyfumaric acid and its salts, or mixtures thereof.

Substantially similar results are obtained if the 2-ethylhexyl methoxycinnamate is replaced, in whole or in part, with octyl methoxycinnamate, butylmethoxydibenzoylmethane, 2-hydroxy- 4-methoxybenzophenone, and mixtures thereof.

Substantially similar results are obtained if the flufenamic acid is replaced, in whole or in part, with hydrocortisone acetate, ibuprofen, naproxen, mefenamic acid, meclofenamic acid, piroxicam, felbinac, 4-(4'-pentyn-3'-one)- 2,6-di-t-butylphenol, 4-(5'-hexynoyl) -2,6-di-t-butylphenol, 4-(S)-(−)-3'-methyl-5'-hexynoyl- 2,6-di-t-butylphenol, 4-(R)-(+)-3'-methyl- 5'-hexynoyl- 2,6-di-t-butylphenol, 4-(3',3 '-dimethoxypropionyl-2,6-di-t-butylphenol, Manjistha, Guggal, and mixtures thereof.

EXAMPLE XIII

A shampoo composition is made by combining the following components.

| Component | Percent by Weight of Composition |
| --- | --- |
| Ammonium Lauryl Sulfate | 12.0 |
| Ammonium Xylene Sulfonate | 2.2 |
| Ammonium Laureth Sulfate | 4.0 |
| NaCl | 0.5 |
| Pyroctone Olamine | 5.0 |
| Octyl Dimethyl PABA | 7.0 |
| Water | 68.1 |
| Perfume and Minor Ingredients | 1.2 |

The ammonium lauryl sulfate, ammonium laureth sulfate, and ammonium xylene sulfonate are first mixed together. The pyroctone olamine and octyl dimethyl PABA and perfume and minor ingredients are added and the resulting mixture is agitated in a Teckmar® Mill set at 70 for 2 minutes at 70° C.

The resulting shampoo composition is added to hair which has been wetted with water, worked through the hair then rinsed out. This allows for deposition of pyroctone olamine and octyl dimethyl PABA to the scalp to inhibit damage caused by acute or chronic UV exposure. Use of an amount of shampoo sufficient to deposit about 0.05 mg/cm$^2$ of pyroctone olamine and 0.05 mg/cm$^2$ of sunscreening agent to the scalp immediately following UV exposure is appropriate. Substantially similar results are obtained if the shampoo is used up to 30 minutes after UV exposure or up to 4 hours prior to UV exposure.

Substantially similar results are obtained if the pyroctone olamine is replaced, in whole or in part, with 2,2 '-dipyridylamine; o-phenanthroline, di-2-pyridylketone; 2-furildioxime; 2,3-bis(2-pyridyl)pyrazine; 2,3-dihydroxybenzoic acid; ethylenediamine-N,N-bis-(2-hydroxyphenylacetic acid), dimethyl ester; 1,1'-carbonyldiimidazole; 1,2-dimethyl- 3-hydroxypyrid-4-one; 2,4,6-tri(2-pyridyl)-1,3,5-triazine; 1-pyrrolidinecarbodithioic acid; diethyldithiocarbamic acid; or Ciclopirox, or mixtures thereof.

Substantially similar results are obtained if the octyl dimethyl PABA is replaced, in whole or in part, with 2-ethylhexyl methoxycinnamate, butylmethoxydibenzoylmethane, 2-hydroxy- 4-methoxybenzophenone, octylmethoxycinnamate, and mixtures thereof.

Substantially similar results are obtained if the flufenamic acid is replaced, in whole or in part, with hydrocortisone acetate, ibuprofen, naproxen, mefenamic acid, meclofenamic acid, piroxicam, felbinac, 4-(4'-pentyn-3'-one)- 2,6-di-t-butylphenol, 4-(5'hexynoyl)-2,6-di-t-butylphenol, 4 -(S)-(−)-3'-methyl-5'-hexynoyl- 2,6-di-t-butylphenol, 4-(R)-(+)-3'-methyl- 5'-hexynoyl- 2,6-di-t-butylphenol, 4-(3',3 '-dimethoxypropionyl)-2,6-di-t-butylphenol, Manjistha, Guggal, and mixtures thereof.

What is claimed is:

1. A method of inhibiting the deleterious effects of chronic ultraviolet light exposure to skin, such deleterious effects including one or more of skin cancer or premature aging as characterized by skin wrinkling, skin yellowing, skin cracking, telangiectasis, solar keratoses, ecchymoses, or lack of elasticity, comprising applying to the skin, prior to exposing the skin to ultraviolet light, a safe and photoprotectively effective amount of a nonsunscreen chelating agent selected from the group consisting of 2,2'-dipyridylamine; 1,10-phenanthroline; di-2-pyridylketone; 2-furildioxime; 2,3-bis(2-pyridyl)pyrazine; 1-hydroxy-4-methyl-6-(2,4,4-trimethylpentyl)-2(1H)-pyridone; 2,3-dihydroxybenzoic acid; ethylenediamine-N,N-bis(2-hydroxyphenylacetic acid), dimethyl ester; 1,1'-carbonyldiimidazole; 1,2-dimethyl-3-hydroxypyrid-4-one; 2,4,6-tri(2-pyridyl)-1,3,5-triazine; 1-pyrrolidinecarbodithioic acid; diethyldithiocarbamic acid; 6-cyclohexyl-1-hydroxy-4-methyl-2(1H)-pyridinone; 2,2'-dipyridyl; 1,2-cyclohexanedione dioxime; 3-hydroxy-2-methyl-4-pyrone; 2,3-bis(2-pyridyl)-5,6-dihydropyrazine; 3-(4-phenyl-2-pyridyl)-5-phenyl-1,2,4-triazine; 5-hydroxy-2-(hydroxymethyl)-4H-pyran-4-one; 2,3-dihydroxypyridine; 2,2'-biquinoline; 2,2'-bipyrazine; 3-(2-pyridyl)-5,6-diphenyl-1,2,4-triazine; 4,4'-dimethyl-2,2'-dipyridyl; 4,5-dihydroxy-1,3-benzene-disulfonic acid; phenyl 2-pyridyl ketoxime; desferrioxamine B; 5,7-dichloro-8-hydroxyquinoline; 2,3-dihydroxynaphthalene; 2,3,5,6-tetrakis-(2'-pyridyl)pyrazine; 2,4-bis(5,6-diphenyl-1,2,4-triazine-3-yl)pyridine; di-2-pyridyl glyoxal; 6-hydroxy-2-phenyl-3(2H)-pyridazinone; 2,4-pteridinediol; 3-(4-phenyl-2-pyridyl)-5,6-diphenyl-1,2,4-triazine; N-benzoyl-N-phenylhydroxylamine; 3-amino-5,6-dimethyl-1,2,4-triazine; 2,6-pyridinedicarboxylic acid; 2,4,5-trihydroxypyrimidine; and 4-(2-amino-1-hydroxyethyl)-1,2-benzenediol.

2. The method of claim 1 wherein the chelating agent is an aromatic amine or a hydroxy aromatic amine selected from the group consisting of 2,2'-dipyridylamine; 1,10-phenanthroline; di-2-pyridylketone; 2,3-bis(2-pyridyl)pyrazine; 2,3-bis(2-pyridyl)-5,6-dihydropyrazine; 1,1'-carbonyldiimidazole; 2,4-bis(5,6-diphenyl-1,2,4-triazine-3-yl)pyridine; 2,4,6-tri(2-pyridyl)-1,3,5triazine; 4,4'-dimethyl-2,2'-dipyridyl; 2,2'-biquinoline; di-2-pyridyl glyoxal; 2,2'-bipyrazine; 3-(2-pyridyl)-5,6-diphenyl-1,2,4-triazine; 3-(4-phenyl-2-pyridyl)-5-phenyl-1,2,4-triazine; 3-(4-phenyl-2-pyridyl)-5,6-di-phenyl-1,2,4-triazine; 2,3,5,6-tetrakis-(2'-pyridyl)pyrazine; 2,6-pyridinedicarboxylic acid; 2,4,5-trihydroxypyrimidine; phenyl 2-pyridyl ketoxime; 3-amino-5,6-dimethyl-1,2,4-triazine; 6-hydroxy-2-phenyl-3(2H)-pyridazinone; 2,4-pteridinediol; 2,2'-dipyridyl; 2,3-dihydroxypyridine; and 5,7-dichloro-8-hydroxyquinoline.

3. The method of claim 1 wherein the chelating agent is a carbonyl or oximate selected from the group consisting of di-2-pyridylketone; 1,1'-carbonyldiimidazole; di-2-pyridyl glyoxal; 2-furildioxime; phenyl 2-pyridylketoxime; and 1,2-cyclohexanedionedioxime.

4. The method of claim 3 wherein the chelating agent is an oximate selected from the group consisting of 2-furildioxime; phenyl 2-pyridylketoxime; and 1,2-cyclohexanedionedioxime.

5. The method of claim 1 wherein the chelating agent is an amine selected from the group consisting of ethylenediamine-N,N-bis-(2-hydroxyphenylacetic acid) dimethyl ester; diethyldithiocarbamic acid; 1-pyrrolidinecarbodithioic acid; and 3-amino-5,6-dimethyl-1,2,4-triazine.

6. The method of claim 1 wherein the chelating agent is a carboxylate, hydroxy acid, hydroxamate or aromatic hydroxy acid selected from the group consisting of 2,3-dihydroxybenzoic acid; ethylenediamine-N,N-bis(2-hydroxyphenylacetic acid) dimethyl ester; 2,6-pyridinedicarboxylic acid; N-benzoyl-N-phenylhydroxylamine; desferrioxamine B; 1-hydroxy-4-methyl-6-(2,4,4-trimethylpentyl)-2(1H)-pyridone; 6-cyclohexyl-1-hydroxy-4-methyl-2(1H)-pyridinone.

7. The method of claim 1 wherein the chelating agent is an enolate selected from the group consisting of 1,2-dimethyl-3-hydroxypyrid-4-one; 3-hydroxy-2-methyl-4-pyrone; 1-hydroxy-4-methyl-6-(2,4,4-trimethylpentyl)-2(1H)-pyridone; and 6-cyclohexyl-1-hydroxy-4-methyl-2(1H)-pyridinone.

8. The method of claim 1 wherein the chelating agent is a phenoxide or catecholate selected from the group consisting of 1-hydroxy-4-methyl-6-(2,4,4-trimethylpentyl)-2(1H)-pyridone; 6-hydroxy-2-phenyl-3(2H)-pyridazinone; 6-cyclohexyl-1-hydroxy-4-methyl-2(1H)-pyridinone; 2,3-dihydroxybenzoic acid; 4,5-dihydroxy-1,3-benzene-disulfonic acid; ethylenediamine-N,N-bis-(2-hydroxyphenylacetic acid) dimethyl ester; 2,3-dihydroxypyridine; 2,4,5-trihydroxypyrimidine; 2,3-dihydroxynaphthalene; 5-hydroxy-2-(hydroxymethyl)-4H-pyran-4-one; 3-hydroxy-2-methyl-4-pyrone; and 4-(2-amino-1-hydroxyethyl)-1,2-benzenediol.

9. The method of claim 1 wherein the chelating agent is selected from the group consisting of 2,2'-dipyridylamine; 1,10-phenanthroline; di-2-pyridylketone; 2-furildioxime; 2,3-bis(2-pyridyl)pyrazine; 1-hydroxy-4-methyl-6-(2,4,4-trimethylpentyl)-2(1H)-pyridone; 2,3-dihydroxybenzoic acid; ethylenediamine-N,N-bis(2-hydroxyphenylacetic acid), dimethyl ester; 1,1'-carbonyldiimidazole; 1,2-dimethyl-3-hydroxypyrid-4-one; 2,4,6-tri(2-pyridyl)-1,3,5-triazine; 1-pyrrolidinecarbodithioic acid; diethyldithiocarbamic acid; 6-cyclohexyl-1-hydroxy-4-methyl-2(1H)-pyridinone; 2,2'-dipyridyl; 1,2-cyclohexanedione dioxime; 3-hydroxy-2-methyl-4-pyrone; 2,3-bis(2-pyridyl)-5,6-dihydropyrazine; 3-(4-phenyl-2-pyridyl)-5-phenyl-1,2,4-triazine; 5-hydroxy-2-(hydroxymethyl)-4H-pyran-4-one; 2,3-dihydroxypyridine; 2,2'-biquinoline; 2,2'-bipyrazine; 3-(2-pyridyl)-5,6-diphenyl-1,2,4-triazine; 4,4'-dimethyl-2,2'-dipyridyl.

10. The method of claim 9 wherein the chelating agent is selected from the group consisting of 2,2'-dipyridylamine; 1,10-phenanthroline; di-2-pyridylketone; 2-furildioxime; 2,3-bis(2-pyridyl)pyrazine; 1-hydroxy-4-methyl-6-(2,4,4-trimethylpentyl)-2(1H)-pyridone; 2,3-dihydroxybenzoic acid; ethylenediamine-N,N-bis-(2-hydroxyphenylacetic acid), dimethyl ester; 1,1'-carbonyldiimidazole; 1,2-dimethyl-3-hydroxypyrid-4-one; 2,4,6-tri(2pyridyl)-1,3,5-triazine; 1-pyrrolidinecarbodithioic acid; diethyldithiocarbamic acid; and 6-cyclohexyl-1-hydroxy-4-methyl-2(1H)-pyridinone.

11. The method of claim 9 wherein the chelating agent is selected from the group consisting of 2,2'-dipyridylamine; 1,10-phenanthroline; di-2-pyridylketone; 2-furildioxime; 2,3-bis(2-pyridyl) pyrazine; 1-hydroxy-4-methyl-6-(2,4,4-trimethylpentyl)-2(1H)-pyridone; 2,3-dihydroxybenzoic acid; and ethylenediamine-N,N-bis-(2-hydroxy-phenylacetic acid), dimethyl ester.

12. The method of claim 9 wherein the chelating agent is 2-furildioxime.

13. The method of claim 1 wherein from about 0.001 mg/cm$^2$ to about 1 mg/cm$^2$ of the chelating agent is applied to the skin.

14. The method of claim 10 wherein from about 0.01 mg/cm$^2$ to about 0.5 mg/cm$^2$ of the chelating agent is applied to skin.

15. The method of claim 1 wherein a safe and photoprotectively effective amount of a sunscreening agent is simultaneously applied to the skin.

16. The method of claim 1 wherein a safe and photoprotectively effective amount of an anti-inflammatory agent is simultaneously applied to the skin.

17. The method of claim 14 wherein from about 0.01 mg/cm$^2$ to about 0.5 mg/cm$^2$ of a sunscreening agent selected from the group consisting of 2-ethylhexyl p-methoxycinnamate, butylmethoxydibenzoylmethane, 2-hydroxy-4-methoxybenzophenone, octyldimethyl p-aminobenzoic acid, the 4-N,N-( 2-ethylhexyl)methylaminobenzoic acid ester of 2,4-dihydroxybenzophenone, the N,N-di-(2-ethylhexyl)-4-aminobenzoic acid ester of 4-hydroxydibenzoylmethane, the 4-N,N-(2-ethylhexyl)methylaminobenzoic acid ester of 4-hydroxydibenzoylmethane, the 4-N,N-( 2-ethylhexyl)methylaminobenzoic acid ester of 2-hydroxy-4-(2-hydroxyethoxy) benzophenone, the 4-N,N-(2-ethylhexyl)methylaminobenzoic acid ester of 4-(2-hydroxyethoxy)dibenzoylmethane, the N-N-di-(2-ethylhexyl)-4-aminobenzoic acid ester of 2-hydroxy-4-(2-hydroxyethoxy)benzophenone, the N,N-di-(2-ethylhexyl)-4-aminobenzoic acid ester of 4-(2-hydroxyethoxy)dibenzoylmethane and mixtures thereof, is simultaneously applied to the skin.

18. A topical photoprotective composition comprising:
(a) a safe and photoprotectively effective amount of a non-sunscreen chelating agent selected from the group consisting of 2,2'-dipyridylamine; 1,10-phenanthroline; di-2-pyridylketone; 2-furildioxime; 2,3-bis(2-pyridyl)pyrazine; 2,3-dihydroxybenzoic acid; ethylenediamine-N,N-bis(2-hydroxyphenylacetic acid), dimethyl ester; 1,1'-carbonyldiimidazole; 2,4,6-tri(2-pyridyl)-1,3,5-triazine; 2,2'-dipyridyi; 1,2-cyclohexanedione dioxime; 3-hydroxy-2-methyl- 4-pyrone; 2,3-bis(2-pyridyl)-5,6-dihydropyrazine; 3-(4-phenyl-2-pyridyl)-5-phenyl- 1,2,4-triazine; 2,3-dihydroxypyridine; 2,2'-biquinoline; 2,2'-bipyrazine; 3-(2-pyridyl)-5,6-diphenyl-1,2,4-triazine; 4,4'-dimethyl-2,2'-dipyridyl; 4,5-dihydroxy-1,3-benzene-disulfonic acid; phenyl 2-pyridyl ketoxime; desferrioxamine B; 5,7-dichloro- 8-hydroxyquinoline; 2,3-dihydroxynaphthalene; 2,3,5,6-tetrakis-(2'-pyridyl)pyrazine; 2,4-bis( 5,6-diphenyl-1,2,4-triazine-3-yl)pyridine; di- 2-pyridyl glyoxal; 6-hydroxy-2-phenyl-3( 2H)-pyridazinone; 2,4-pteridinediol; 3-( 4-phenyl-2-pyridyl)-5,6-diphenyl-1,2,4-triazine; N-benzoyl-N-phenyl-hydroxylamine; 3-amino-5,6-dimethyl- 1,2,4-triazine; 2,4,5-trihydroxypyrimidine; and 4-( 2-amino-1-hydroxyethyl)-1,2-benzenediol; and
(b) a safe and effective amount of a topical carrier comprising a safe and effective amount of an emollient.

19. The composition of claim 18 wherein said chelating agent is selected from the group consisting of 2,2'-dipyridylamine; 1,10-phenanthroline; di- 2-pyridylketone; 2-furildioxime; 2,3-bis(2-pyridyl) pyrazine; 2,3-dihydroxybenzoic acid; ethylenediamine-N,N-bis-(2-hydroxyphenylacetic acid) dimethyl ester; 1,1'-carbonyldiimidazole; and 2,4,6-tri( 2-pyridyl)-1,3,5-triazine.

20. The composition of claim 18 wherein said chelating agent is selected from the group consisting of 2,2'-dipyridylamine; 1,10-phenanthroline; di- 2-pyridylketone; 2-furildioxime; 2,3-bis(2-pyridyl) pyrazine; [1-hydroxy- 4-methyl-6-( 2,4,4-trimethylpentyl)2(1H)-pyridone;] 2,3-dihydroxybenzoic acid; and ethylenediamine-N,N-bis-(2-hydroxyphenylacetic acid), dimethyl ester.

21. The composition of claim 18 wherein the chelating agent is 2-furildioxime.

22. The composition of claim 19 which comprises from about 1% to about 10% of the chelating agent.

23. The composition of claim 18 which additionally comprises a safe and photoprotectively effective amount of a sunscreening agent.

24. The composition of claim 18 which additionally comprises a safe and photoprotectively effective amount of an anti-inflammatory agent.

25. The composition of claim 22 which additionally comprises from about 1% to about 20% of a sunscreening agent, wherein the sunscreening agent is selected from the group consisting of 2-ethylhexyl p-methoxycinnamate, butylmethoxydibenzoylmethane, 2-hydroxy-4-methoxybenzophenone, octyldimethyl p-aminobenzoic acid, the 4-N,N-( 2-ethylhexyl)methylaminobenzoic acid ester of 2,4-dihydroxybenzophenone, the N,N-di-( 2-ethylhexyl)-4-aminobenzoic acid ester of 4-hydroxydibenzoylmethane, the 4-N,N-(2-ethylhexyl)methylaminobenzoic acid ester of 4-hydroxydibenzoylmethane, the 4-N,N-( 2-ethylhexyl)methylaminobenzoic acid ester of 2-hydroxy-4-( 2-hydroxyethoxy)benzophenone, the 4-N,N-(2-ethylhexyl)methylaminobenzoic acid ester of 4-(2hydroxyethoxy)dibenzoylmethane, the N-N-di-(2-ethylhexyl)-4aminobenzoic acid ester of 2-hydroxy-4-( 2-hydroxyethoxy)benzophenone, the N,N-di-(2-ethylhexyl)-4-aminobenzoic acid ester of 4-(2-hydroxyethoxy)dibenzoylmethane and mixtures thereof.

* * * * *

UNITED STATES PATENT AND TRADEMARK OFFICE
CERTIFICATE OF CORRECTION

PATENT NO. : 5,487,884

DATED : January 30, 1996

INVENTOR(S) : Bissett, et al.

It is certified that two errors appear in the above-identified patent and that said Letters Patent is hereby corrected as shown below:

In Column 39, line 28 (ninth line of Claim 18) "2,2'-dipyridyi" should read --2,2'-dipyridyl--.

In Column 40, lines 11 and 12 (fourth and fifth lines of Claim 20) delete "[1-hydroxy-4-methyl-6-(2,4,4-trimethylpentyl)2(1H)-pyridone;]".

Signed and Sealed this

Sixth Day of May, 1997

Attest:

BRUCE LEHMAN

Attesting Officer

Commissioner of Patents and Trademarks